(12) United States Patent
Srinivasan et al.

(10) Patent No.: US 8,518,467 B2
(45) Date of Patent: *Aug. 27, 2013

(54) FIBER SEPARATION FROM GRAIN USING ELUSIEVE PROCESS

(75) Inventors: Radhakrishnan Srinivasan, Mississippi State, MS (US); Vijay Singh, Savoy, IL (US); Ravi Challa, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 537 days.

This patent is subject to a terminal disclaimer.

(21) Appl. No.: 12/704,481

(22) Filed: Feb. 11, 2010

(65) Prior Publication Data

US 2010/0206780 A1 Aug. 19, 2010

Related U.S. Application Data

(63) Continuation-in-part of application No. 11/180,475, filed on Jul. 13, 2005, now Pat. No. 7,670,633.

(60) Provisional application No. 60/604,160, filed on Aug. 23, 2004.

(51) Int. Cl.
*B07B 13/08* (2006.01)
(52) U.S. Cl.
USPC ............ 426/482; 426/479; 426/618; 209/645
(58) Field of Classification Search
USPC .......................... 426/482, 479, 618
See application file for complete search history.

(56) References Cited

U.S. PATENT DOCUMENTS

| 2,808,152 | A | * | 10/1957 | Kaufman et al. | ............ 209/238 |
| 3,236,740 | A | * | 2/1966 | Smith et al. | ................... 435/161 |
| 3,506,119 | A | * | 4/1970 | Leschonski et al. | ....... 209/139.1 |
| 7,670,633 | B2 | * | 3/2010 | Srinivasan et al. | ............ 426/482 |

FOREIGN PATENT DOCUMENTS

JP 07227300 * 8/1995

OTHER PUBLICATIONS

English translation of the specification of JP 07227300 published Aug. 1995.*

* cited by examiner

*Primary Examiner* — Anthony Weier
(74) *Attorney, Agent, or Firm* — Butler, Snow, O'Mara, Stevens & Cannada PLLC

(57) ABSTRACT

Methods, devices, and compositions relating to processed grain products are shown for ground corn flour, soybean meal, cottonseed meal, and wheat middlings. An exemplary method shown is a fiber separation process for the ethanol industry corn products of Distillers Dried Grains (DDG) and Distillers Dried Grains with Solubles (DDGS) resulting from the widely used dry grind technology. A shown process and apparatus allows the removal and separate recovery of fiber-reduced products with expanded potential for use as a non-ruminant feed product in addition to the removal and separate recovery of a fiber-enriched product. The fiber enriched and fiber reduced products each have uses in the feed industry. The specific processes, devices, and compositions shown are readily adaptable to feed mills.

15 Claims, 18 Drawing Sheets

FIBER SEPARATION FROM GRAIN USING ELUSIEVE PROCESS

CROSS-REFERENCES TO RELATED APPLICATIONS

This application is a CONTINUATION IN PART of application Ser. No. 11/180,475, which was filed on Jul. 13, 2005 now U.S. Pat. No. 7,670,633. Application Ser. No. 11/180,475 claims the benefit of U.S. Provisional Application No. 60/604,160 by Srinivasan and Singh, filed Aug. 23, 2004. Each application is incorporated herein by reference in its entirety.

STATEMENT REGARDING FEDERALLY SPONSORED RESEARCH OR DEVELOPMENT

This invention was made with government support under 0212821 awarded by the Cooperative State Research, Education, and Extension Service, USDA.

FIELD OF THE INVENTION

The present invention is generally directed toward a method of separating fiber from grain products including corn flour, soybean meal, and cotton seed meal.

BACKGROUND OF THE INVENTION

A significant agricultural commodity, corn (maize), is processed for several purposes, including industrial uses in addition to human and animal consumption. An increasingly important industrial use of corn is the production of ethanol which is in turn used, for example, as a fuel. Due to increased demands, ethanol production from corn is expected to rise rapidly, with projections indicating a doubling of production capacity within the next few years.

A widespread method of ethanol production utilizes the Dry Grind process and modified versions thereof; see FIGS. 1 and 2. Ethanol producers often prefer the Dry Grind process to an alternative method known as Wet Milling (FIG. 3) due to the simplicity, low initial capital investment, and lower operating costs associated with Dry Grind. The Dry Grind process is currently estimated to yield about 70% of the ethanol produced in the United States. These trends of increased ethanol production and acceptance of Dry Grind are forecasted to continue.

Corn can be described as comprising several components. The four main components include starch, also referred to as the carbohydrate or sugar component; protein; fat, also referred to as oil; and fiber. In the Dry Grind process, starch is converted to ethanol. First, the corn is ground into corn flour. Next, water is added to the corn flour, and the resulting slurry is treated in the presence of enzymes to convert the sugars to glucose. Glucose is fermented using yeast to produce crude ethanol. The crude ethanol-water mixture is treated by distillation, yielding purified ethanol.

From the distillation step, the solids or "grains" coming out of the distilling column are called Distillers Grains. The water component resulting from the distillation column is evaporated, and the resulting "solubles" are mixed with the Distillers Grains; this combination is conventionally known as Distillers Grains with Solubles. Alternatively, the Distillers Grains are not mixed with the Distillers Solubles. Finally, the Distillers Grains or Distillers Grains with Solubles are dried, generating Distillers Dried Grains (DDG) or Distillers Dried Grains with Solubles (DDGS). DDGS consist largely of corn minus the starch component; in other words, DDGS have the remaining components of protein, fat, fiber, and some unconverted starch. Physically, it is a solid powdery or aggregate material with color hues ranging from a bright golden yellow to brown.

Dry Grind processing in the ethanol production industry thus yield DDGS as a major byproduct. Directly correlating with the increase in ethanol production, the supply of DDGS as a commodity will likely increase proportionately. As a commodity, DDGS has constrained economic value. For example, the typically high fiber content of DDGS restricts its applicability as a feed product. DDGS is highly suitable as an animal feed for ruminant animals such as cattle which can naturally digest the fiber. Non-ruminant animals, however, are generally less able to digest high fiber DDGS. DDGS as commercially produced is also found to be variable in its nutrient composition such as protein, fat, fiber, ash, or starch content (see Belyea, 2004). This variability can diminish the value of DDGS when business consumers consider certain criteria, such as minimum protein and/or fat content proportions, for a feed product to be of importance.

Attempts have been made to improve processes and products of ethanol production from corn. See U.S. Pat. No. 6,254,914 by Singh et al., issued Jul. 3, 2001; United States Patent Applications 20030104587 by Verser et al., published Jun. 5, 2003; 20030180415 by Stiefel et al., published Sep. 25, 2003; and 20030232109 by Dawley et al., published Dec. 18, 2003.

In Singh, et al., 2002, the possibility of using air aspiration to remove fiber from DDGS was investigated. A kilogram sample of DDGS was placed on a 20-mesh screen and aspirated with an air jet at a pressure of approximately 2.8 atmospheres using a procedure similar to that of Eckhoff et al., 1996. The study showed limited success for aspiration in recovering fiber from DDGS and in recovering phytosterol compounds which are plant sterols that may be useful in lowering cholesterol levels. Aspirating DDGS samples produced by the dry-grind ethanol process did not yield an aspirated fraction that was significantly enriched in phytosterols. Aspiration of DDGS resulted in enrichment of oil and protein content and reduction of the neutral detergent fiber in the "residual" DDGS fraction (original DDGS after the removal of the aspirated fraction; note that terminology in Singh et al., 2002 may not necessarily correspond to present usage herein). The reduction in fiber content of this residual DDGS, however, was not found to be large enough to make a practical feedstuff for non-ruminants because the fiber levels were significantly above levels typically found in non-ruminant diets (Singh et al., 2002).

An invention that improves the economic value of grain products such as DDG or DDGS is highly desirable. DDGS can be improved by one or more of decreasing the fiber content, enriching the protein and/or fat content, and standardizing the nutrient content of the commodity. Reduction of the high fiber content can open up the use of DDG or DDGS as a feed product to non-ruminant animals and help maintain the supply and demand balance of the commodity. As a side benefit, a fiber-enriched product of the invention can itself contribute value to an ethanol production plant as an additional useful product of the DDGS processing and ultimately of corn. Some examples of valuable products potentially available from the fiber-enriched products include corn fiber gum and corn fiber oil. The phytosterol-containing oil in the corn fiber (corn fiber oil) has potential use as a natural low-density lipoprotein (LDL) lowering nutraceutical (see Moreau R A et al., 1999, Cereal Chemistry 76(3):449-451;

Singh V et al., 2003, Cereal Chemistry 80(2):118-122). A fiber-enriched product can also be useful for dietary needs or as a laxative.

Ground corn flour is a major ingredient in diets for swine and poultry, which do not digest fiber very well. There exists a demand for a method of increasing the digestible energy of corn flour and thus increasing value of corn flour as an ingredient in non-ruminant diets.

There also exists a demand for protein-rich grain products. The production of oilseeds, such as soybean and cottonseed in the U.S. was 93 million tons in 2008, an increase of 16% from 2007 (USDA-NASS, 2008). Most of the increased oilseed production was attributed to increased soybean production. Soybean meal, or SBM, is the material that remains after extracting oil from soybean flakes. Oil is extracted by either solvent extraction of ground flakes or by expeller process where the beans are heated and squeezed (SMIC, 2008). Soybean meal is considered a prominent source of plant protein for poultry diet. It has high protein content, and it is the highest in energy content of all common oil seeds. The demand for protein-rich products is increasing. The poultry industry uses a significant portion of U.S. soybean meal. There exists a need to increase the protein and energy contents in each pound of SBM. The high protein quality and consistency of nutrient content makes soybean meal a preferred choice over other feeds for poultry diets.

Cottonseed meal (CSM) is also produced after solvent extraction of oil from cottonseed kernels or by mechanical extraction; most cottonseed meal produced in the U.S. is produced by solvent extraction (SMIC, 2008). Soybean meal has 48% of protein, whereas cottonseed meal has 41%. With 41% of protein content, cottonseed meal is an excellent source of protein for a variety of animal species.

Wheat middlings (midds), a byproduct after extracting flour from wheat and durum during milling, are a useful feed for cattle (NDSU, 1999). Wheat middlings include screenings, bran, germ, shorts, offal and flour rejects. Crude protein content in wheat middling is typically 17% to 18% on a dry matter basis (NDSU, 1999).

SUMMARY OF THE INVENTION

The present invention addresses problems related to the state of the art in agricultural technologies involving grain products. Specifically, we disclose a method for separating grain byproducts into fiber-rich and low-fiber products that have use. This optimizes the value of the grains and results in less waste. Our methods are applicable to DDGS, corn flour, soybean meal, cottonseed meal, and wheat middlings.

The following definitions are applicable.

When used herein, the term "classifying" refers to a separation or differentiation of a material into fractions based on one or more characteristics of a particle or aggregate of the material such as density, shape, size, and/or weight. The material can be heterogeneous with respect to the components of composition of material; for example, the material can have components of fiber, protein, fat, and starch. Alternatively, the material can be homogenous or heterogeneous, regarding the composition, but heterogeneous in another aspect, namely that particles of the material can vary in size, shape, density, electrostatic charge, or other parameter. In an example, the material is substantially all fiber; however, the fiber component can have larger and smaller fiber particles. The term is intended to broadly encompass and relate to classification systems, processes, and devices as known in the art. In a preferred embodiment, the term refers to air classification. In a specific embodiment, a subset of classifying is elutriation. In a specific embodiment, a subset of classifying is aspiration.

When used herein, the term "elutriation" refers to a purification, separation, or removal process. In an embodiment, the process can effect the separation of particles. In a preferred embodiment, the separation can be on the basis of one or more physical properties such as particle size, density, shape, weight, or other property. In a particular embodiment, such a process can be achieved by a washing or treatment with a fluid flow, where a fluid can be air. In a preferred embodiment, the process utilizes ambient air to separate a starting material into heavy and light fractions.

When used herein, the term "fraction" refers to a separated or differentiated portion of a starting substance. The term is intended to encompass a yet further differentiated portion of a fraction or subfraction.

When used herein, the term "heavier fraction" or "heavy fraction" can generally be understood by one of ordinary skill in the art. In an embodiment, the term refers to a material which can or does tend to settle downward during a classification process. In a particular embodiment, the material settles at the bottom of an air elutriation column. Other equivalent terms in an embodiment can be referred to as heavy material, heavier material, or residual fraction.

When used herein, the term "lighter fraction" or "light fraction" can generally be understood by one of ordinary skill in the art. In an embodiment, the term refers to a material which can or does tend to be carried upward during a classification process. In a particular embodiment, the material is carried by air toward the top of an elutriation column in an elutriation process. Other equivalent terms in an embodiment can be referred to as light material or lighter material. Another equivalent term in an embodiment is fiber fraction, indicating an instance where such fraction has an enriched fiber content relative to an earlier material.

When used herein, the term "sieving" refers to a separation process which is based on the difference in the size of particles of a material. In a particular embodiment, the process uses a mechanical sieve or screen. For example, a sieve can be in the form of a regular or irregular mesh, a perforated solid surface, a three-dimensional matrix, or a column of differential porosity. The term encompasses a process separating a larger or coarser particle from a smaller or finer particle. In an embodiment, separation is achieved with the assistance of equipment using vibratory motion.

When used herein, the term "Distillers Dried Grains with Solubles" or DDGS broadly refers to a non-fermentable byproduct of the corn kernel. In an embodiment, the term includes DDGS such as conventionally generated by the ethanol production industry (see FIG. 1). When produced from corn, DDGS is generally a combination of protein, fat, fiber, and unconverted starch. The term is intended to encompass modified DDGS such as generated from the modified dry grind ethanol process (see FIG. 2). The term can be interpreted as understood in the art and is intended to encompass definitions such as the feed ingredient definition according to the Association of American Feed Control Officials, including the product obtained after removal of ethyl alcohol by distillation from the yeast fermentation of corn by condensing and drying at least three-fourths of the solids of the resultant whole stillage. When used herein, note that DDGS is a processed corn product itself while serving as a starting material for further processing to generate additional processed corn products.

When used herein, the term "Distillers Dried Grains" or DDG broadly refers to a non-fermentable byproduct of the corn kernel. In an embodiment, the term includes DDGS such as conventionally generated by the ethanol production industry. The term can be interpreted as understood in the art and is intended to encompass definitions such as the feed ingredient definition according to the Association of American Feed Control Officials, including the material obtained after the removal of ethyl alcohol by distillation from the yeast fermentation of corn by separating the resultant coarse grain fraction of the whole stillage and drying it.

When used herein, the term "processed grain product" refers to a material that is available for consumption by animals or humans and for industrial purposes. In an embodiment, the term includes DDGS and DDG of the corn ethanol production industry. In other embodiments, the term includes legumes (e.g. soybeans), barley, wheat, sorghum, and other materials (e.g. other oilseeds).

When used herein, the term "enriched" refers to an attribute of an intermediate output or ending material that is at least partially increased in a component relative to a starting material. For example, an output material can be fiber-enriched, protein-enriched, or fat-enriched.

When used herein, the term "reduced" refers to an attribute of an output material that is at least partially decreased or depleted in a component relative to a starting material. For example, an output material can be fiber-reduced, protein-reduced, or fat-reduced.

When used herein, the term "Residual DDGS" or "Residual product" refers in an embodiment to an output material with a fiber content amount that is lesser than that found in an original DDGS material from which the output is derived. In a specific embodiment, this material can have expanded use as a feed product, for example, in non-ruminant animals in addition to ruminant animals.

When used herein, the term "fiber-enriched fraction" or "fiber-enriched product" refers in an embodiment to an output material with a fiber content amount that is greater than that found in an original DDGS material from which the output is derived.

When used herein, the term "output" or "output product" refers generally to a product material generated from an input or starting material or from a previous output material. In an embodiment, an output can be a fraction. In an embodiment, an output can be an intermediate stage product or an end or final product. In a particular embodiment, the term can refer to either residual DDGS or a fiber-enriched fraction.

When used herein, the term "phytosterol" refers to one or more plant-based sterol compounds. The term is intended to be understood as known in the art and can encompass the definition by the National Cancer Institute, including a plant-based compound that can compete with dietary cholesterol to be absorbed by the intestines, resulting in lower blood cholesterol levels; phytosterols may have some effect in cancer prevention.

The following abbreviations are applicable: DDGS, Distillers Dried Grains with Solubles; ADF, acid detergent fiber; NDF, neutral detergent fiber.

In an embodiment, the invention provides a method for processing an agricultural grain product by a combination of two separation techniques, classifying and sieving. One or more fractions produced by the method can be used as independent products or variously combined. In an embodiment, a desired fraction or combination of fractions can be determined so as to yield a high, optimal, or maximal economic return based on a projected or actual commercial market value for a given fraction or combination of fractions.

In an embodiment, the invention provides a method for processing an agricultural grain product by a single separation technique. In a particular embodiment, the technique is classifying or sieving.

In an embodiment, the processing methods of the invention can include a step of grinding or milling to generate a material with certain size parameters, e.g. a uniform size or a material with an average particle size or threshold particle size. In a particular embodiment, one or more size parameters are selected so as to facilitate separation such as by size. For example, grinding or milling is used to prepare a material for sieving or another separation technique. In an embodiment, the milled or ground material is subjected to air classification alone in order to separate the fiber.

In an embodiment, upstream processing in dry grind plant is carried out such that size and characteristics of DDGS facilitate use of only one separation technique to separate fiber from DDGS. In an embodiment, grinding/milling of corn, size of syrup balls, and other governing parameters in the process are controlled such that a single separation technique of either air classification or sieving is effective in separating fiber from DDGS. In an embodiment, air classification, sieving or a combination of the two is used to separate fiber from milled corn flour in the upstream of the dry grind processing instead of separating fiber from DDGS.

In an embodiment, the invention provides a method of separating a material by electrostatic precipitation. For example, a first particle with a first size and first electrostatic charge can be separated from a second particle with a second size and second electrostatic charge. In an embodiment, the first size of the first particle is larger than the second size of the second particle, and vice versa in another embodiment (likewise for the electrostatic charge). The size and charge parameters along with other physical properties can be exploited to facilitate separation of the material. An electrostatic charge can be induced in a classifying column, sieving device, or gravity flow slide/incline (wherein the slide/incline can be porous to function simultaneously as a sieve).

Nutritionists favor animal feeds with a high protein content that are highly digestible. Fiber separation from these animal feeds could increase the protein content and hence increase the value of the feed. In this study, a combination of sieving and air classification was evaluated for fiber separation from SBM, CSM and WM.

The present inventors have surprisingly discovered that the invention can be specifically applied to solving the problem of how to increase the utilization of a coproduct of the ethanol industry, DDGS. In the example of DDGS, it has been found that the fiber components of the DDGS are generally less dense than the non-fiber components (here, 'non-fiber' does not necessarily mean completely devoid of fiber for a given particle or aggregate as found in commercial of DDGS). Hence, when air is passed through the DDGS, a substantial portion of the fiber component is carried along by the air. Some non-fiber, however, also can get carried along by the air because the forces experienced by large-sized fiber particles and small-sized non-fiber particles are the same. The non-fiber material can then be subjected to a further purification step of separation by size of particles. In an application of the invention, elutriation and sieving conditions can be adjusted to enhance a desired yield or degree of purity for a fiber or non-fiber output fraction. The availability of these new output fractions from DDGS thus expands its utilization as a coproduct of the ethanol industry.

The invention provides a method of generating at least one fiber-enriched fraction and at least one fiber-reduced fraction from a processed grain product starting material, comprising:

a) classifying said grain product into a first fraction and a second fraction, wherein said first fraction has a lighter material and said second fraction has a heavier material reduced in fiber relative to said starting material; and b) separating by size said first fraction into first and second subfractions, wherein said first subfraction has a larger particle size and is enriched in fiber relative to said starting material and said second subfraction has a smaller particle size and is reduced in fiber relative to said starting material; thereby generating at least one fiber-enriched fraction and at least one fiber-reduced fraction from a processed grain product. In an embodiment, the invention provides this method further comprising combining said second fraction with said second subfraction, thereby forming a combined material reduced in fiber relative to said starting material.

In an embodiment, the method generates at least one fiber-reduced fraction enriched in protein content, fat content, or both protein and fat content.

In a preferred embodiment, the processed grain product is Distillers Dried Grains with Solubles, DDGS. In another preferred embodiment, the processed grain product is Distillers Dried Grains, DDG. In an embodiment, the processed grain product is derived from one or more of legumes (e.g. soybeans), barley, wheat, and sorghum.

In an embodiment where the processed grain product is DDGS or analogous material for other products, the methods, compositions, and devices of the invention are applicable for said DDGS or analogous material produced by any modification in the beginning of a dry-grind process. Exemplary modifications include a quick germ process, a quick fiber process, an enzymatic wet-milling process, the use of new enzymes, combinations of the foregoing, and other upstream changes in the dry-grind process.

In embodiments of methods of the invention, classifying uses gravity air elutriation. In embodiments, separation based on particle size difference is performed by sieving.

The invention provides a method of generating at least one fiber-enriched fraction and at least one fiber-reduced fraction from a processed grain product starting material, comprising: a) separating by size said grain product into a first fraction and a second fraction, wherein said first fraction has a larger particle size, and said second fraction has a smaller particle size; and b) a first classifying, wherein said first fraction is classified so as to yield a first subfraction of a lighter material enriched in fiber relative to said starting material and a second subfraction of a heavier material reduced in fiber relative to said starting material; thereby generating a fiber-enriched fraction and a fiber-reduced fraction from a processed grain product. In an embodiment, this method comprises combining said second fraction of smaller particle size and said second subfraction, thereby forming a combined material reduced in fiber relative to said starting material.

In an embodiment, the invention provides a method comprising a second classifying, wherein said second fraction (smaller particle size) is classified so as to yield a third subfraction of a lighter material enriched in fiber and a fourth subfraction of a heavier material reduced in fiber. In a particular embodiment, this method further comprises combining said first subfraction with said third subfraction, thereby forming a combined material enriched in fiber relative to said starting material. In another particular embodiment, this method further comprises combining said second subfraction with said fourth subfraction, thereby forming a combined material reduced in fiber relative to said starting material.

In an embodiment, the invention provides a method of generating at least one fiber-enriched fraction and at least one fiber-reduced fraction from a processed grain product starting material, comprising: a) separating by size said grain product into a first fraction and a second fraction, wherein said first fraction has a larger particle size, and said second fraction has a smaller particle size; and b) a first classifying, wherein said second fraction is classified so as to yield a first subfraction of a lighter material enriched in fiber and a second subfraction of a heavier material reduced in fiber; thereby generating a fiber-enriched fraction and a fiber-reduced fraction from a processed grain product. In an embodiment, this method further comprises combining said first fraction with said first subfraction, thereby forming a combined material enriched in fiber relative to said starting material.

In another embodiment, the method further comprises a step c), a second classifying, wherein said first fraction is classified so as to yield a third subfraction of a lighter material enriched in fiber and a fourth subfraction of a heavier material reduced in fiber. In a particular embodiment, the method further comprises combining said first subfraction with said third subfraction, thereby forming a combined material enriched in fiber relative to said starting material. In another particular embodiment, the method further comprises combining said second subfraction with said fourth subfraction, thereby forming a combined material reduced in fiber relative to said starting material.

The invention provides a method of classifying DDGS, comprising elutriation of DDGS so as to yield a lighter fraction enriched in fiber and a heavier fraction reduced in fiber.

The invention provides a gravity elutriation device for separating fiber from a processed grain product, comprising a vertical flow column, an air inlet connected to said column, a blower operatively connected to said air inlet so as to introduce a fluid flow of air into said column; a feed inlet connected to said column at a point located above said air inlet so as to allow said fluid flow to act as a force on a substance passing from said inlet into said column; a feeder operatively connected to said feed inlet for introducing said processed grain product; and a lighter fraction collection reservoir disposed with respect to said column to receive a portion of said product.

In an embodiment, the elutriation device comprises a heavier fraction or residue collection reservoir proximal to said bottom end, wherein said heavier fraction collection reservoir serves to contain a residual component of said product subjected to said fluid flow.

The invention provides a fiber removal and harvesting apparatus comprising a fluid-flow classifying device, a sieving device, and a conveyor for receiving an output from said classifying device and transporting said output to said sieving device. The invention provides a fiber removal and harvesting apparatus comprising a fluid-flow classifying device, a sieving device, and a conveyor for receiving an output from said sieving device and transporting said output to said classifying device.

The invention provides DDG and DDGS compositions. The invention provides a DDGS composition comprising a fiber content amount. In an embodiment, the fiber content amount is selected from the group consisting of up to about 40%, up to about 35%, up to about 30%, up to about 25%, up to about 20%, up to about 15%, up to about 10%, and up to about 5%. The invention provides a DDGS composition comprising a fiber content amount of about 10% or less. An embodiment of the invention is a DDGS composition comprising a fiber content of from about 5% to about 10%. Embodiments of the invention include a DDGS composition comprising a fiber content percentage selected from the group consisting of about 9%, about 8%, about 7%, about 6%, about 5%, about 4%, about 3%, and about 2%.

An embodiment of the invention is a DDG or DDGS composition enriched in fiber relative to a starting material prepared by methods of the invention. An embodiment of the invention is a DDG or DDGS composition reduced in fiber relative to a starting material prepared by methods of the invention.

The invention provides a feed product or feed product supplement digestible by non-ruminant animals. In a particular embodiment, the feed product or feed product supplement comprises processed DDGS wherein said DDGS has a fiber content selected from the group consisting of about 10% or less, about 8% or less, and about 6% or less.

The invention provides a method of modifying ethanol production so as to integrate a DDG or DDGS fiber removal process comprising the steps of: a) classifying said DDG or DDGS so as to yield a lighter fraction and a heavier fraction; b) sieving said DDG or DDGS so as to yield a larger particle size fraction and a smaller particle size fraction; c) characterizing at least one said lighter fraction, heavier fraction, larger fraction, and smaller fraction regarding fiber content; and d) removing at least one of said lighter fraction, heavier fraction, larger fraction, and smaller fraction characterized as having enriched fiber content relative to a starting material; thereby modifying ethanol production so as to integrate a DDG or DDGS fiber removal process.

The invention provides a method of processing a DDG or DDGS starting material, comprising; a) determining whether a first processing step should be a procedure of classifying or separating by size, and a second processing step should be the procedure not chosen for the first processing step; and b) selecting at least one classification parameter or at least one sieving parameter depending on said determining step. In an embodiment, at least one classification parameter is selected from the group consisting of air velocity rate, treatment time, a physical property of an average starting material, and a physical property of a specific batch of starting material. In an embodiment, a sieving parameter is selected from the group consisting of a pore size, agitation frequency, sieving capacity, treatment time, a physical property of an average starting material, and a physical property of a specific batch of starting material. In an embodiment, the method further comprises one or more further separation steps, wherein a step can be classifying or sieving.

In an embodiment, one or more steps follow an initial combination of sieving and classification (e.g. elutriation). For example, an entire process can comprise sieving, classifying, and sieving; another entire process comprises sieving, classifying, sieving, and classifying; and so forth. Optionally the order of steps in embodiments of the invention is such that classifying (e.g. elutriation) precedes sieving.

In an embodiment, classifying employs an air classification system. In a particular embodiment, the air classification system is selected from the group consisting of: static cyclone, cyclone classifiers, single or multi-stage dynamic classifiers, cross-flow classifiers, spiral separators, high energy dispersion classifiers, and turbine classifiers (single and multiple wheel). In an embodiment, an air classification system can employ a packed bed, fluidized bed, spouted bed, or other approach to facilitate or enhance particle manipulation. In an embodiment, an air classification system can incorporate features of a uniform aerodynamic deduster that has been described for use in dust particle separation (See such described by Yuanhui Zhang of the University of Illinois; e.g. Zhang et al., 1998).

An embodiment of the invention is a fiber-enriched composition wherein said composition comprises a fiber content selected from the group consisting of about 10% or more, about 20% or more, about 30% or more, about 40% or more, about 50% or more, and about 60% or more.

An embodiment of the invention is a residual fraction composition wherein said composition comprises a crude protein content selected from the group consisting of about 50% or less, about 40% or less, about 30% or less, about 20% or less, and about 10% or less.

An embodiment of the invention is a residual fraction composition wherein said composition comprises a crude fat content selected from the group consisting of about 40% or less, about 30% or less, about 20% or less, and about 10% or less.

In an embodiment, a fiber-enriched fraction or composition generated from DDGS or DDG comprises corn fiber gum or corn fiber oil. In a particular embodiment, a fiber-enriched fraction or composition comprises phytosterols. In a preferred embodiment, the phytosterols are present in a pharmaceutically effective or nutraceutically effective amount.

The invention provides methods, devices, and compositions relating to the removal of fiber from DDGS products.

Embodiments of the invention are applicable to DDGS products of the ethanol industry, for example, the DDGS product of the conventional dry grind ethanol process and the modified DDGS product of the modified dry grind ethanol process such as described by Singh et al., 2001.

In preferred embodiments of the invention, processed DDG or DDGS maintains the bright golden yellow color often associated with a DDG or DDGS product regarded as being of high quality.

In an embodiment, a process, device, or composition is readily adaptable to a modern ethanol production plant. For example, a process or device of the invention can be added as a module to a current end point in a plant without substantially interfering with an upstream item or activity.

BRIEF DESCRIPTION OF THE DRAWINGS

Further advantages of the invention will become apparent by reference to the detailed description of preferred embodiments when considered in conjunction with the drawings.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The invention may be further understood by the following non-limiting examples.

EXAMPLE 1

Method of Removing Fiber from DDGS

Figure 4:
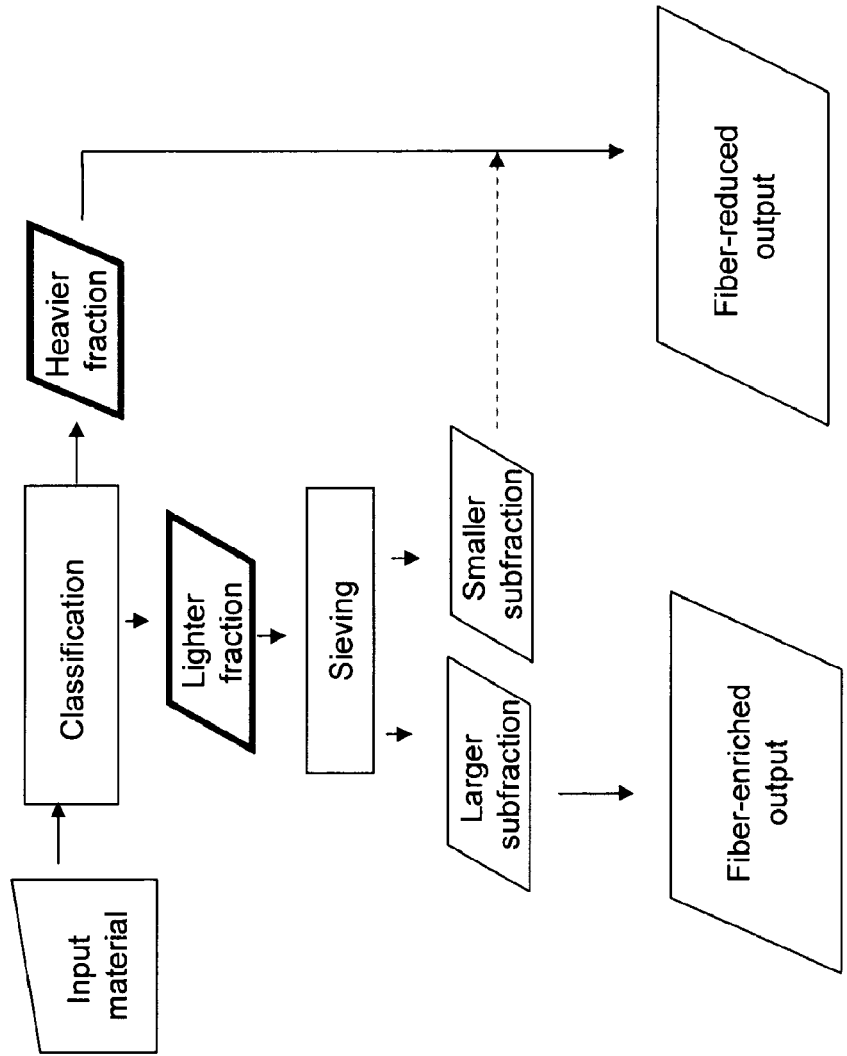
FIG. 4. Flowchart of fiber removal process with elutriation then sieving.
Figure 5:
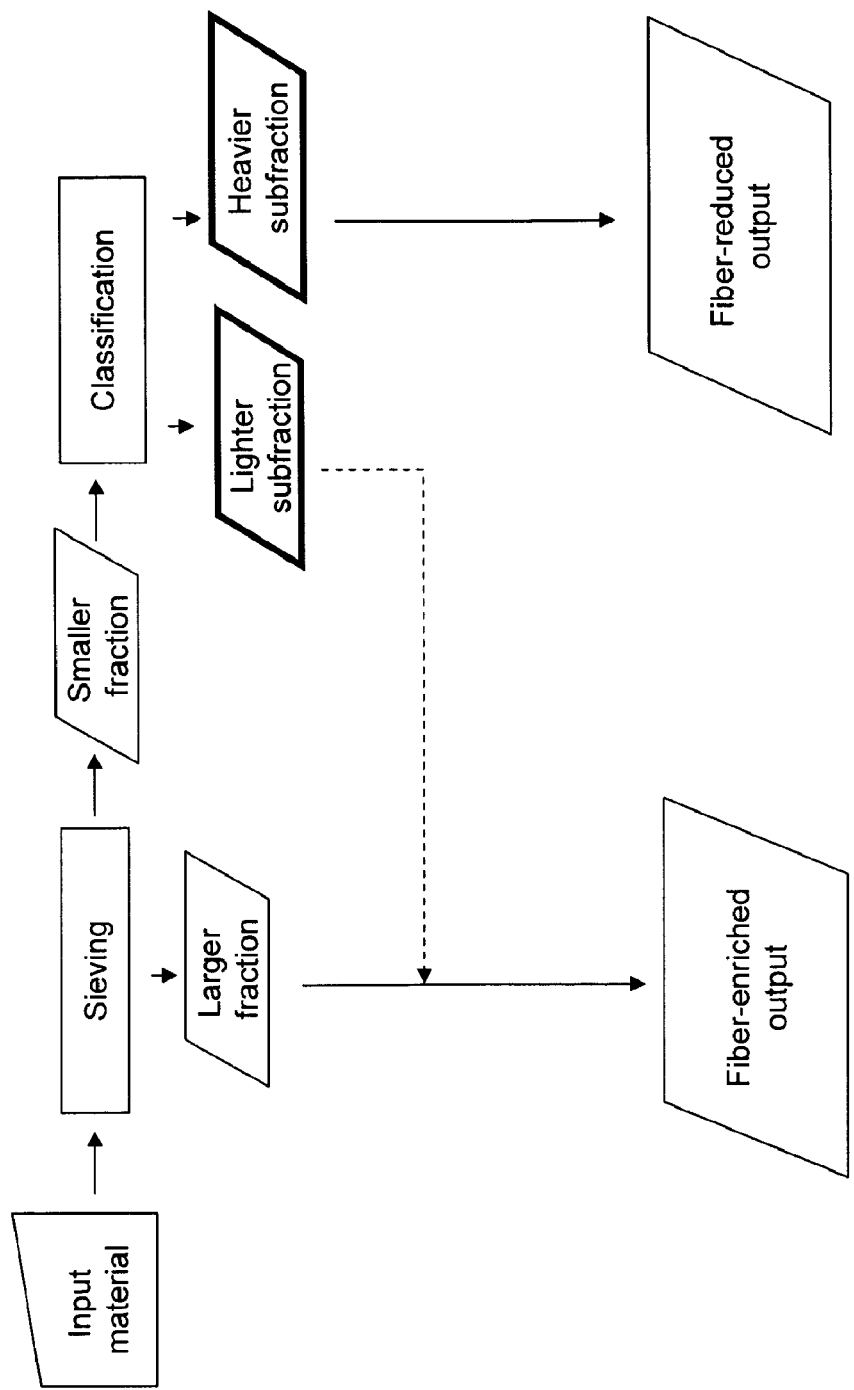
FIG. 5. Flowchart of fiber removal process with sieving then elutriation.

FIG. 4 illustrates a flow chart of a fiber removal process. Input material is first subjected to classification, such as by gravity air elutriation. This separates the input material into heavier and lighter fractions. The lighter fraction is then sieved into a larger subfraction and a smaller subfraction. The initial heavier fraction can be combined with the smaller subfraction from sieving to yield a fiber-reduced output. The larger subfraction from sieving yields a fiber-enriched output.

Figure 1A:
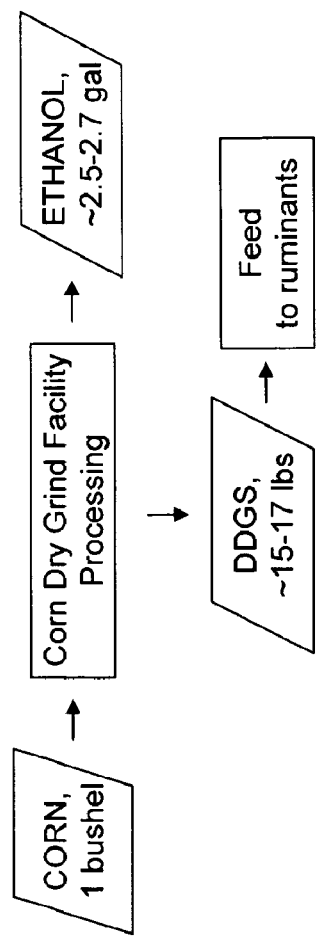
FIGS. 1A and 1B. Overview and schematic of the conventional dry grind ethanol process.
Figure 1B:
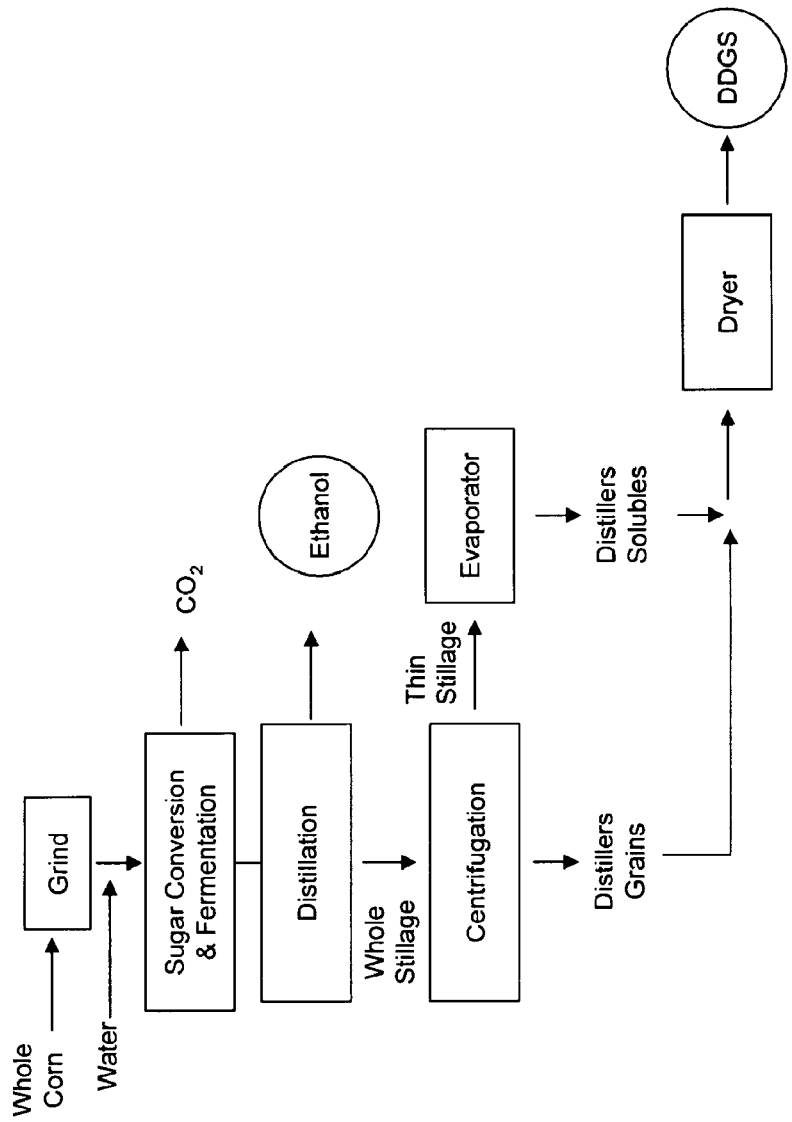
Figure 2:
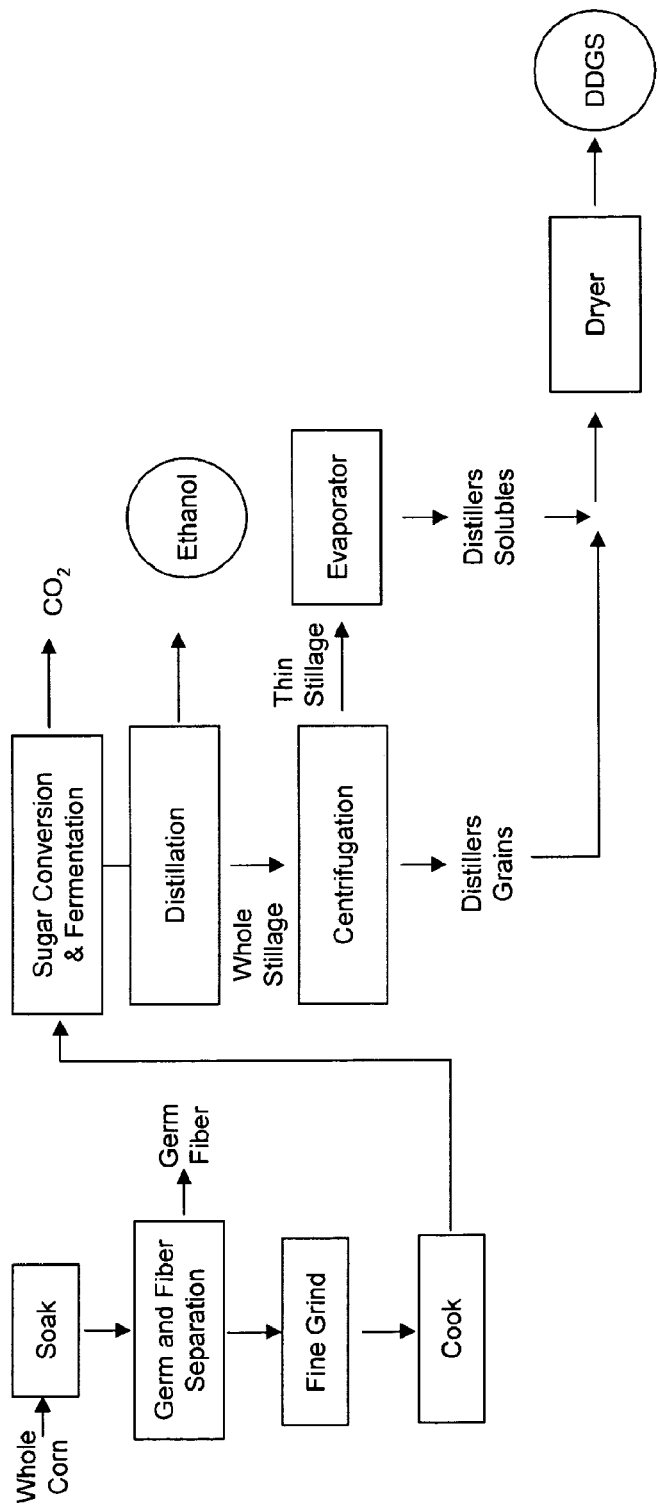
FIG. 2. Schematic of the modified dry grind ethanol process.
Figure 3:
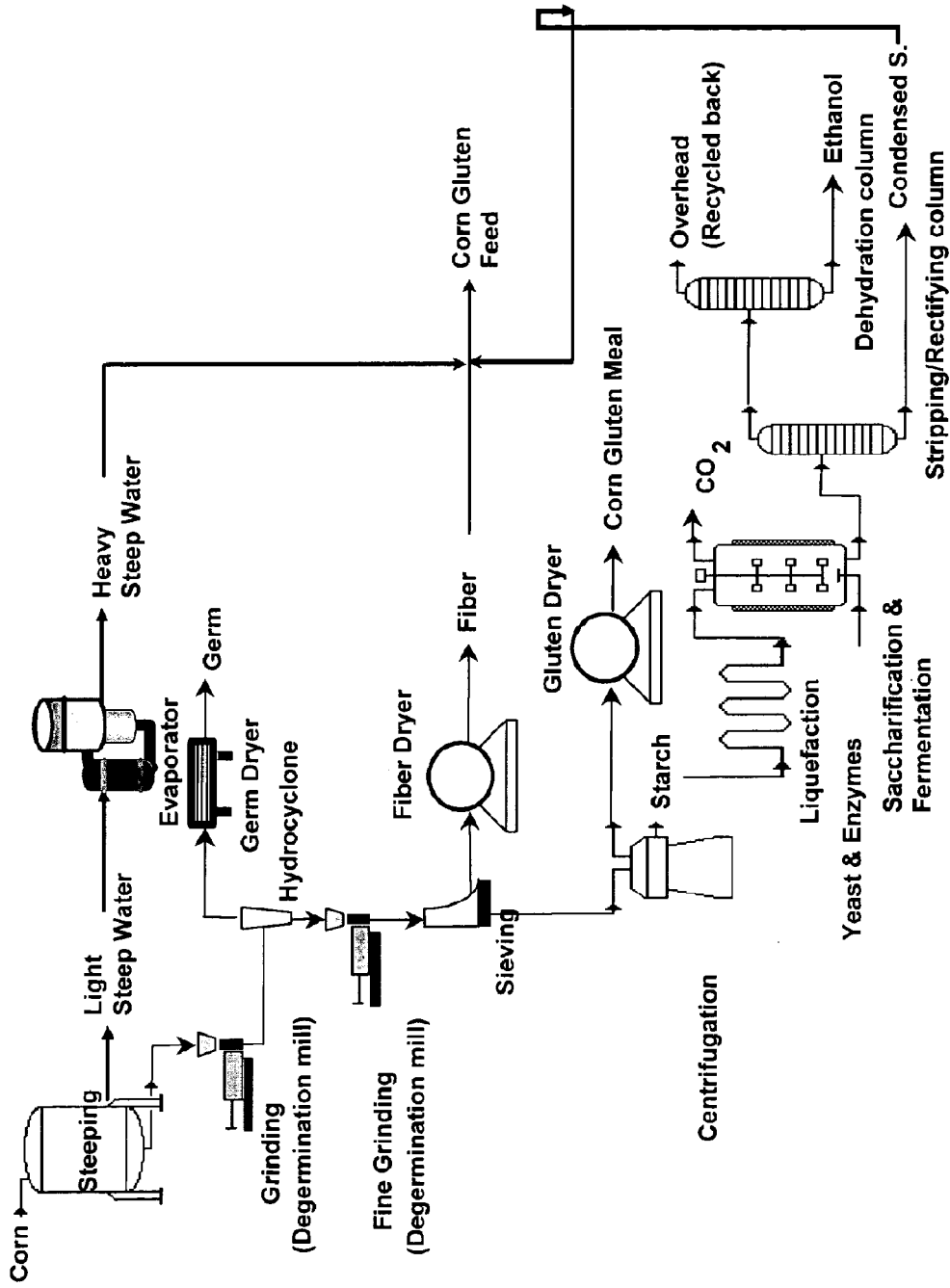
FIG. 3. Schematic of the corn wet milling process.

In a particular example, the input material is DDGS. DDGS is conventionally produced in an ethanol processing plant using the Dry Grind process. See FIG. 1. In an embodiment of the invention, the fiber content of conventionally produced DDGS is reduced to yield an enhanced DDGS. This enhanced DDGS can be used as feed product for non-ruminant agricultural animals, such as swine and poultry, in addition to still being suitable for ruminants. Additionally, enhanced DDGS can be used as a feed or supplement for non-agricultural animals including companion animals such as dogs and cats. Furthermore, enhanced DDGS can also be used as a human food, for example in gourmet human cuisine.

During elutriation, an initial DDGS batch is exposed to the fluid flow force of an air stream. The force acts to separate or differentiate the DDGS into a heavier fraction and a lighter fraction. The heavier fraction is reduced in fiber content. The heavier fraction can also be referred to as "DDGS residue." The lighter fraction is enriched in fiber content.

It has surprisingly been found that some particles of non-fiber components, however, are carried along by the air force despite their relatively greater density; these tend to be smaller particles with a correspondingly lighter absolute weight. The lighter fraction is thus significantly enriched in fiber but also comprises non-fiber particle components of the original DDGS starting material. Without wishing to be bound by a particular theory, it is believed that an explanation for the makeup of the elutriated lighter fraction is as follows. As the original DDGS is subjected to forces in elutriation, the forces experienced by large-sized light particles and small-sized denser particles are the same. The air force may discriminate on the basis of a combination of factors such as particle mass, weight, volume, density, and shape. Generally, many particles of the fiber component of DDGS are larger in size and lighter in weight than particles of non-fiber components of DDGS.

After elutriation, one or more characteristics of fiber and non-fiber particles are exploited by size separation, such as by screening or sieving, to obtain further products. The further products include an enriched, cleaner or purer fiber product and a fiber-reduced product. Screening the lighter fraction material that comes out with the air, therefore, allows separate recovery of fiber and non-fiber material. The combination of elutriation and sieving is found to be effective in generating reduced-fiber DDGS and a fiber-enriched product from DDGS starting material.

During sieving, the larger particles that do not pass through the sieve are enriched or relatively pure fiber. Smaller particles that are sieved are reduced in fiber and enriched in protein and/or fat content. Sieving the elutriated lighter fraction thus yields a larger particle size subfraction and a smaller particle size subfraction. The sieved smaller particle size subfraction can be added to the DDGS residue. The combination of the sieved smaller subfraction and the DDGS residue can be referred to as "enhanced DDGS." Alternatively, DDGS residue alone can be referred to as "enhanced DDGS."

The DDGS residue can optionally be sieved before or after being combined with the sieved smaller particle size subfraction.

The elutriated lighter fraction can be used as a source of enriched fiber. Following sieving of this lighter fraction, the larger particle size subfraction can be used as a source of fiber that is yet further enriched in its fiber proportion relative to starting material.

Figure 9:
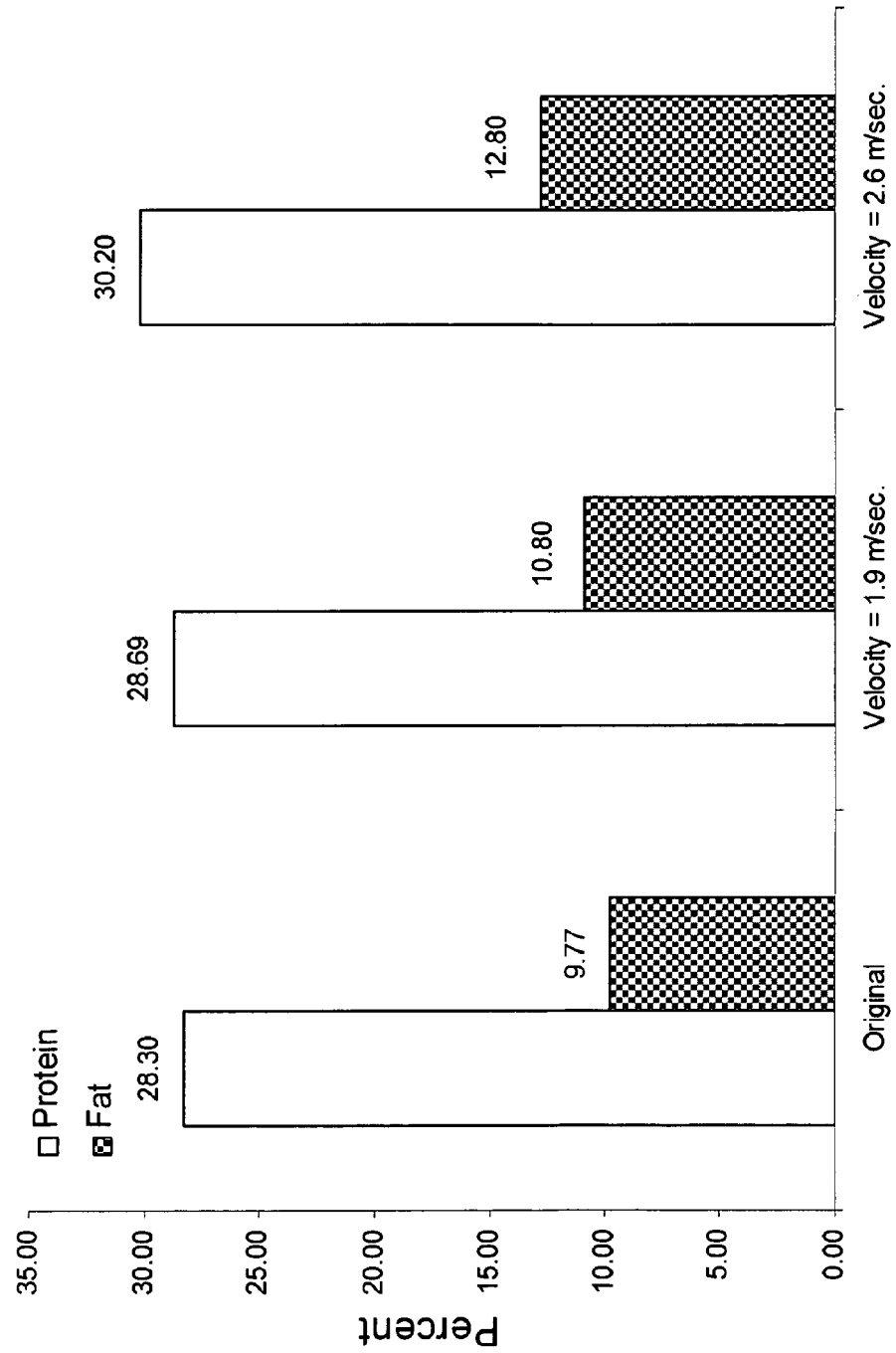
FIG. 9. Graph illustrating protein and fat content data in heavy fractions harvested from processing DDGS by elutriation at different air flow rates.

In a specific example, original DDGS material was subjected to gravity air elutriation. The air velocity was 1.9 m/s (meters per second) or 2.6 m/s. The protein and fat content from heavy fractions were analyzed. See FIG. 9. The original DDGS material had an initial protein content of 28.30% and fat content of 9.77%. Under the condition of air velocity at 1.9 m/s, the recovered heavy fraction had a protein content of 28.69% and a fat content of 10.80%. Under the condition of air velocity at a rate of 2.6 msec, the recovered heavy fraction had a protein content of 30.20% and a fat content of 12.80%. The increase in air velocity, thus, contributed to an increased percentage of both protein and fat in the recovered heavy fraction. Calculations of protein and fat content were performed based on a percentage of dry matter.

Figure 10:
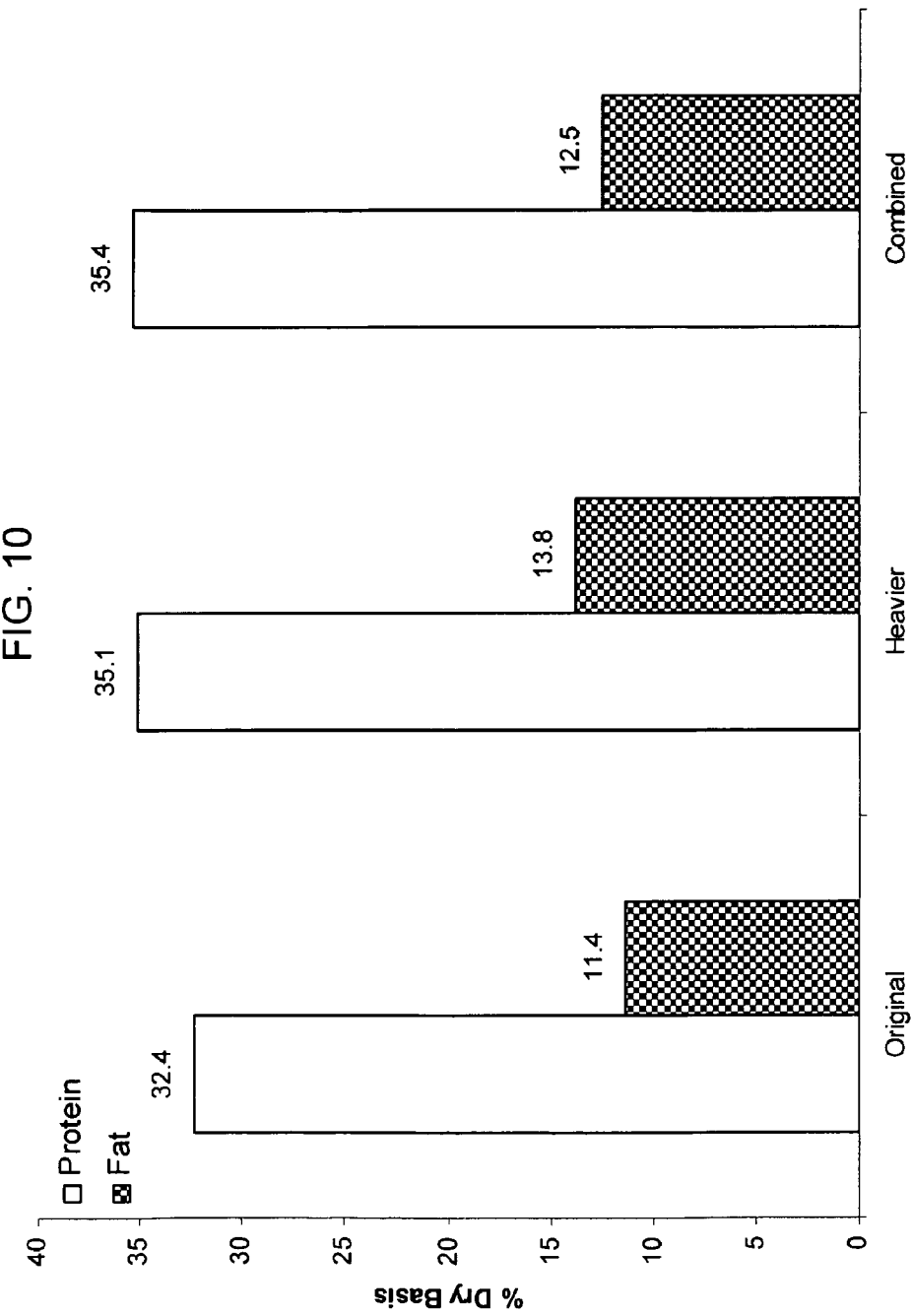
FIG. 10. Graph of protein and fat content data of DDGS outputs after elutriation at an air velocity of 2.6 meters per second.

For data In FIG. 10, original DDGS material was processed by elutriation, then sieving. First, gravity air elutriation was performed at an air velocity rate of 2.6 m/s, separating DDGS into lighter and heavier fractions. Next, the lighter fraction was sieved to generate a larger particle size subfraction and a smaller particle size subfraction. A sample of the heavier fraction was analyzed. Material referred to as "combined" here was prepared by combining the heavier fraction with the smaller particle size subfraction from sieving. Samples from both the heavier and combined material demonstrated increases in protein and fat content on a percentage of dry matter basis relative to the original DDGS material. The heavier or combined DDGS material is, therefore, enriched in protein and fat content.

Figure 11:
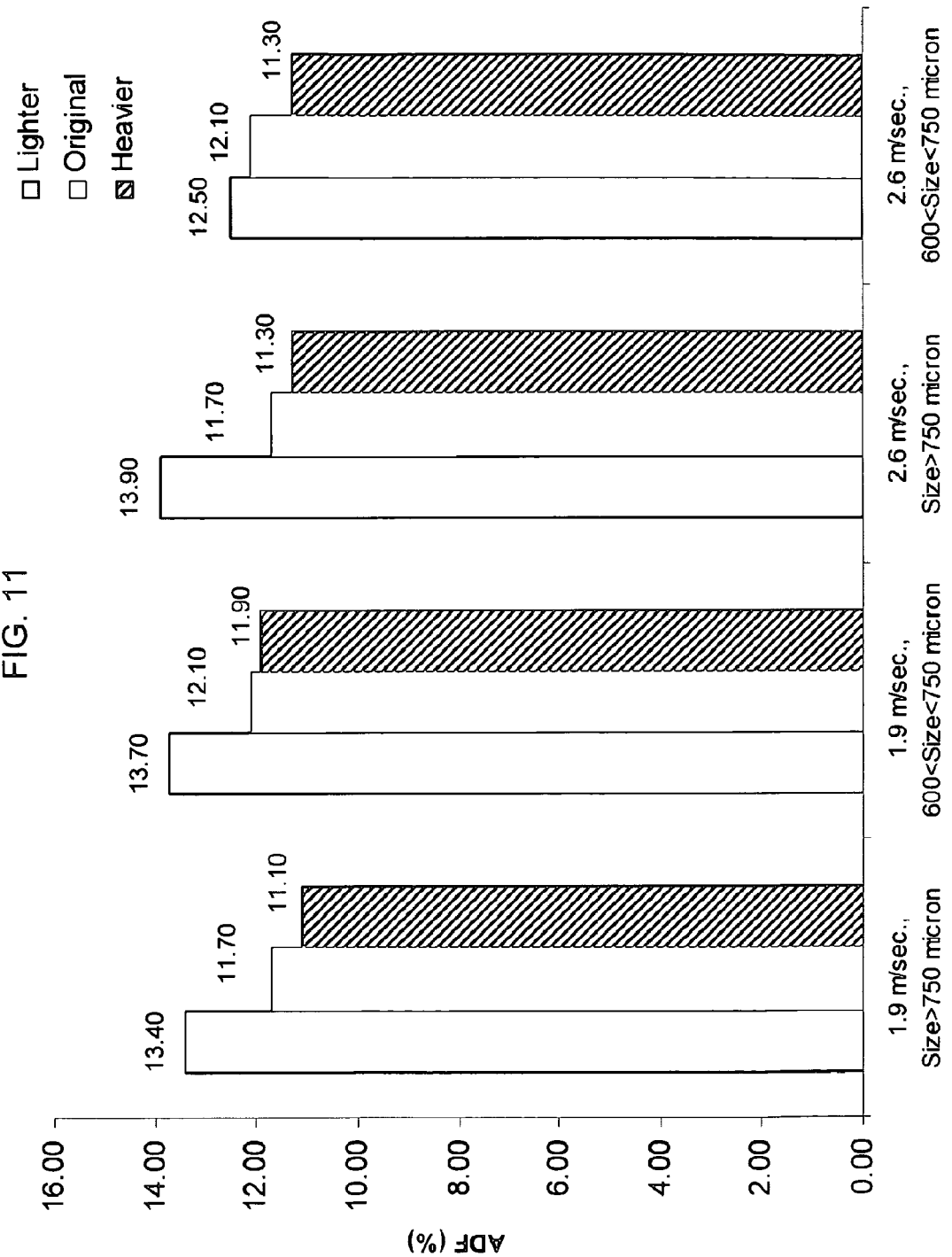
FIG. 11. Graph illustrating acid detergent fiber (ADF) percentage data from processed DDGS products of original, lighter, and heavier fractions resulting from elutriation at various air flow rates followed by sieving of various particle size ranges relative to a size X: (a) X>750 micron at 1.9 msec; (b) 600<X<750 micron at 1.9 msec; (c) X>750 micron at 2.6 msec; and (d) 600<X<750 micron at 2.6 msec.

The combination of elutriation and sieving was effective in generating from original DDGS material a fiber-enriched lighter fraction and a fiber-reduced heavier fraction. FIG. 11 indicates data from acid detergent fiber measurements (ADF %) of DDGS material processed under certain combinations of conditions. Elutriation was performed at air velocity rates of 1.9 or 2.6 m/s to generate lighter and heavier fractions from DDGS original material. Sieving was performed using pore sizes of 600 microns and 750 microns. Relative to original material, lighter fraction material was consistently found to be higher or enriched in fiber content, and heavier fraction material was consistently found to be lower or reduced in fiber content. At the same flow rate, lighter fraction material not passing through a sieve opening of 750 microns consistently had a fiber content greater than material with a particle size of between 600 and 750 microns. Sieving was performed using pore sizes of 600 microns, 750 microns, or 850 microns.

Figure 12:
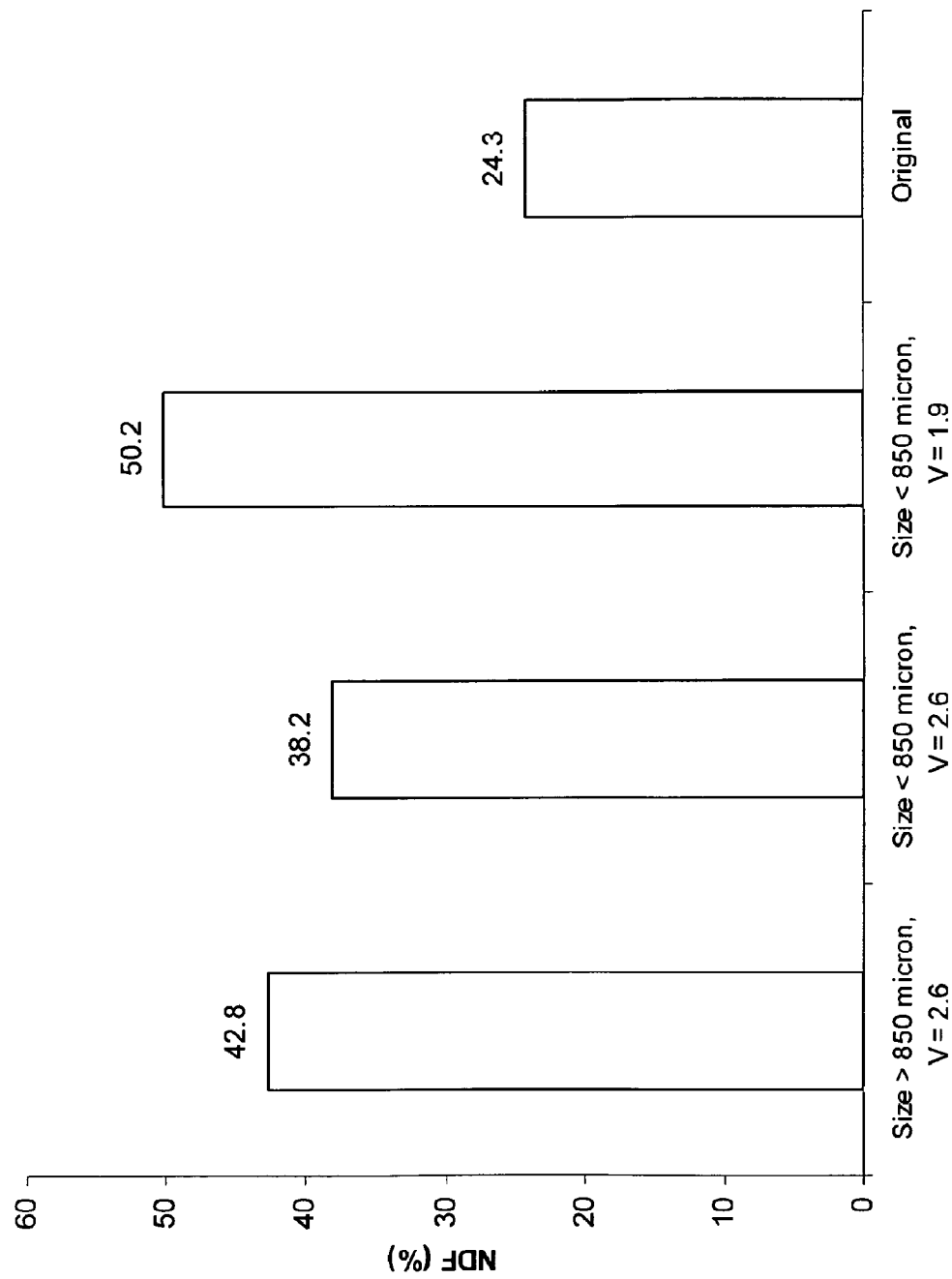
FIG. 12. Graph illustrating neutral detergent fiber (NDF) percentage data from processed DDGS products of original and lighter fractions of various particle size ranges.
Figure 13:
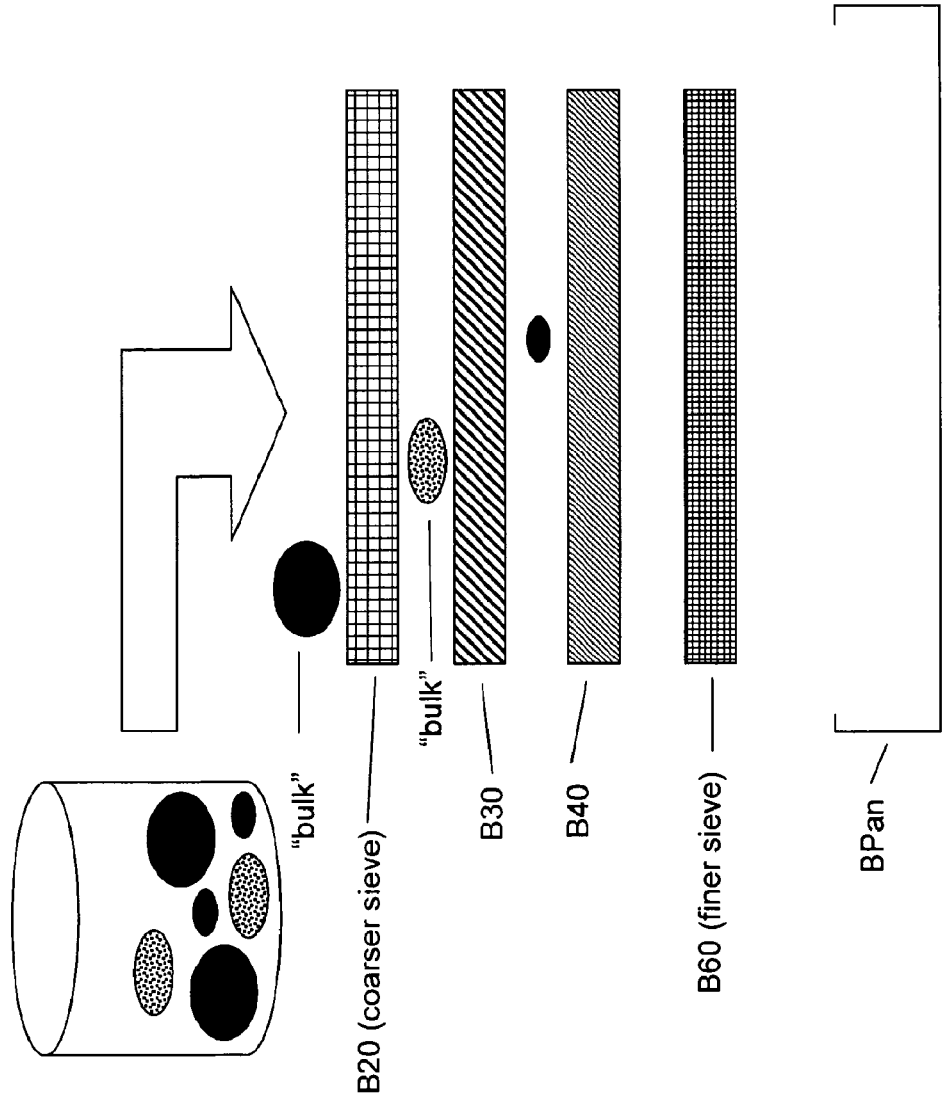
FIG. 13. Schematic of tiered sieving screens.

An experiment was performed to assess optimal velocity conditions for fiber enrichment of lighter fractions. FIG. 12 shows results of neutral detergent fiber percentage measurements for processed DDGS samples. Elutriation was performed at air velocity rates of 1.9 or 2.6 m/s, and lighter fractions were collected. Next, sieving was performed with an opening size of 850 microns. A lower flow rate resulted in a lighter fraction with a significantly enriched fiber content of more than double that of the original starting material. At the elevated flow rate of 2.6 m/s, an enhancement of fiber content was also observed but not as great as at the lower air velocity. Larger sieved particles (>850 micron) of the lighter fraction obtained at 2.6 m/s had greater fiber content than smaller sieved particles (<850 micron).

EXAMPLE 2

Elutriation Apparatus

Figure 6:
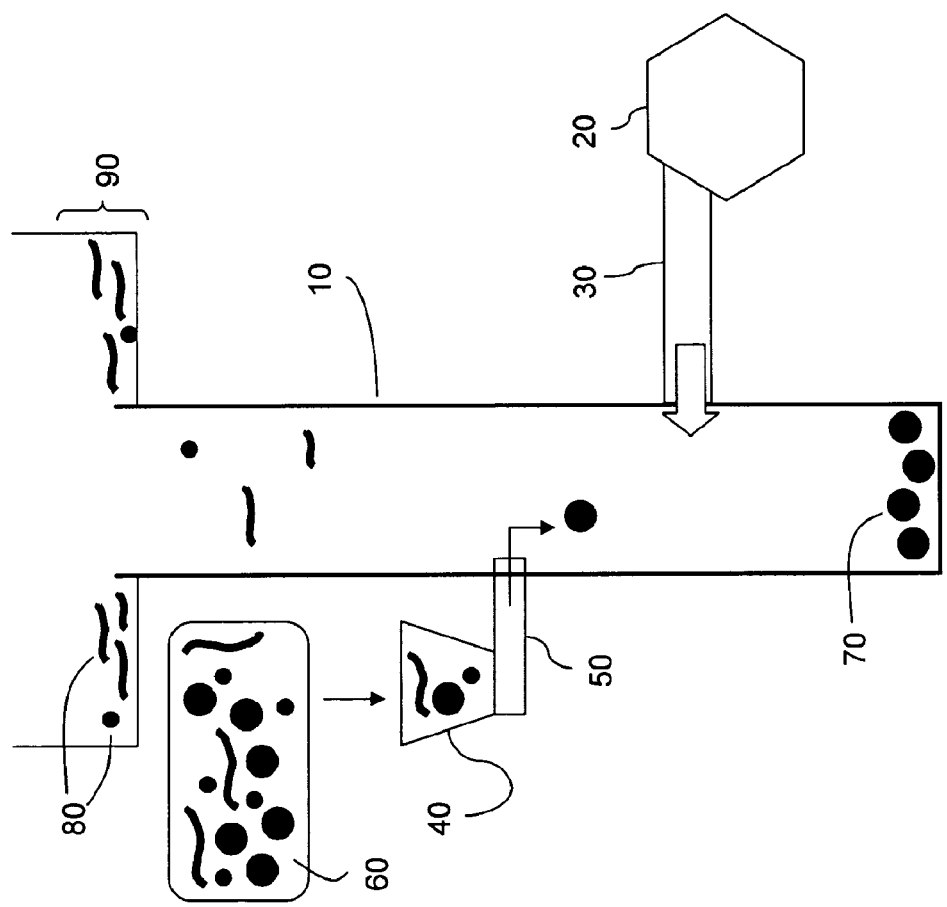
FIG. 6. Schematic of elutriation apparatus.
Figure 7:
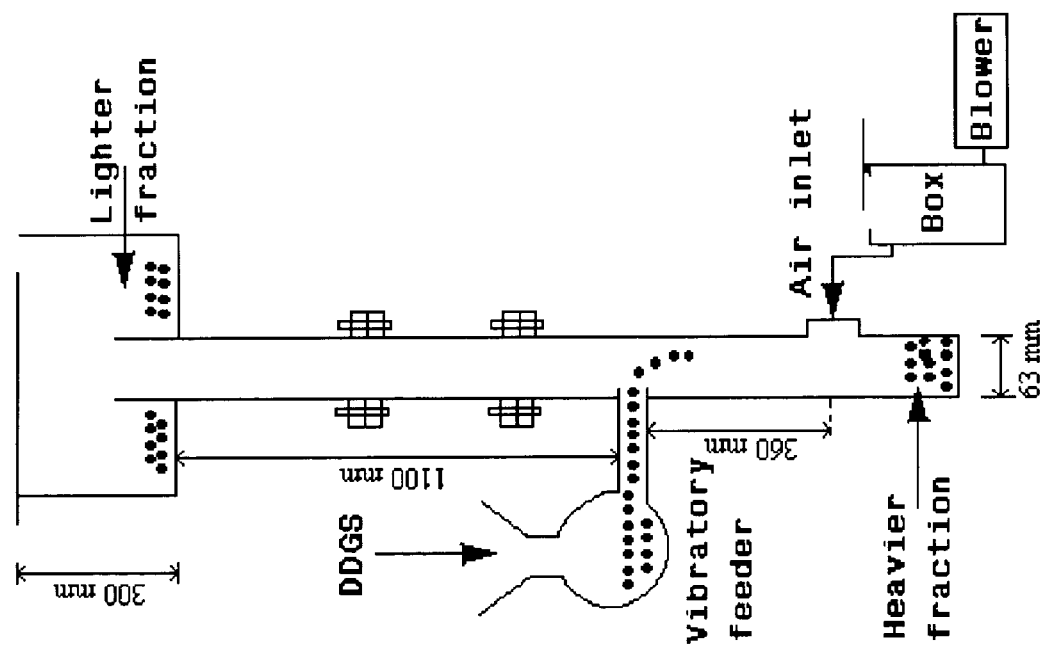
FIG. 7. Schematic of a specific embodiment of an elutriation apparatus used for DDGS.
Figure 8:
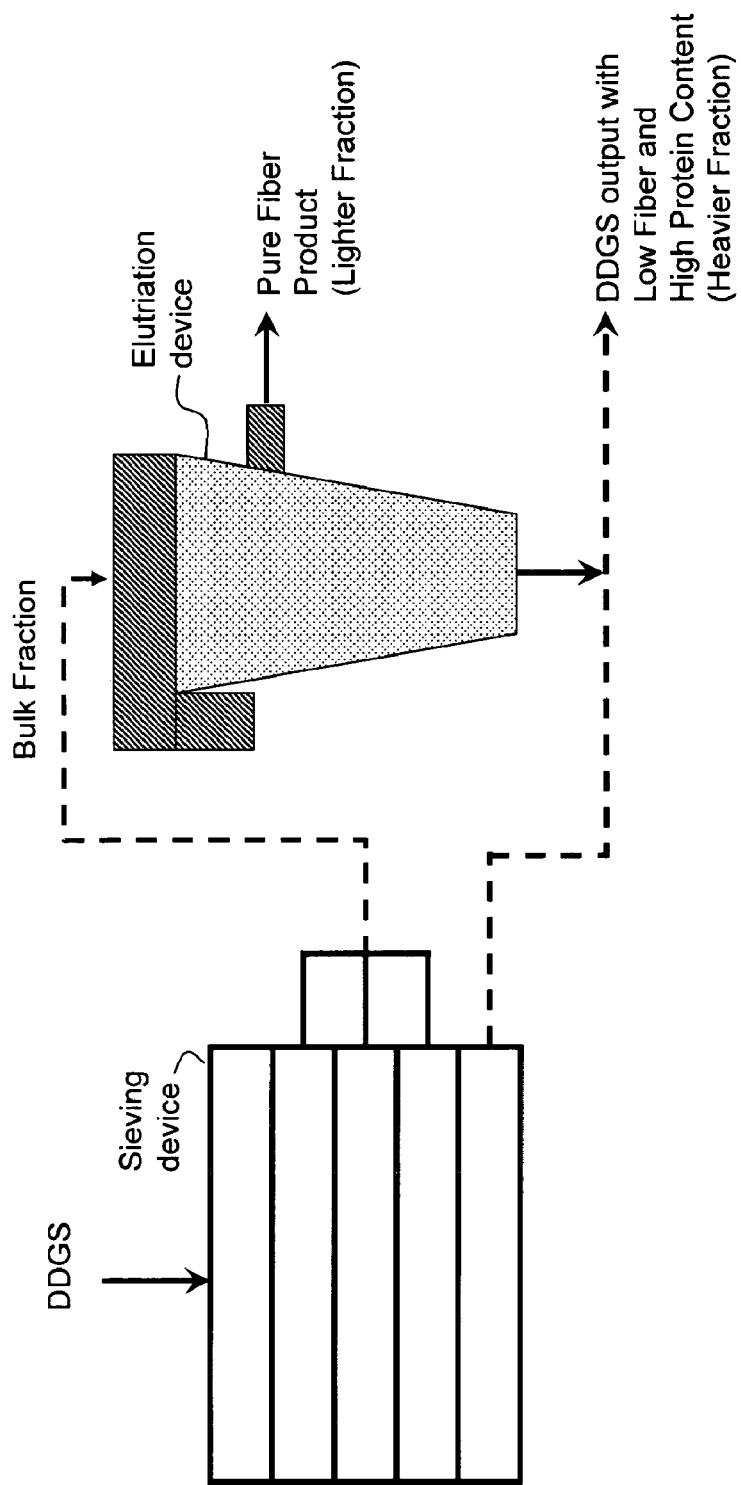
FIG. 8. Schematic of a specific embodiment of a method of processing DDGS.

See FIG. 6. An elutriation column 10 is connected to a fan or air blower 20 via an air inlet 30. A feeder 40 is connected to column 10 via a feeder inlet 50. Input material 60, comprised of light components and heavy components, is introduced to column 10 using feeder 40. Output residue or heavier fraction 70 collects at the bottom end of column 10. Output lighter fraction 80 is carried by fluid flow to one or more collection reservoirs 90. See also FIG. 7.

A feeder is used as known in the art. For example, the feeder can be a vibratory feeder, auger, hopper, conveyer, or dumper container optionally mechanized. Used in several examples herein, a preferred vibratory feeder is POWDERTEC 3090 Sample Mill. A blower used in several examples herein is Dayton Model No. 2C701.

The elutriation column used in certain examples herein has a height of 61 inches above the feeding inlet and a diameter of 2.5 inches.

EXAMPLE 3

Sieving Apparatus

A sieving apparatus is used as known in the art. In several examples herein, the separator used was a Sweco Vibro-Energy Separator, Model No. LS185883.

EXAMPLE 4

Elutriation in a Horizontal Flow Column

In an embodiment, the elutriation is performed using a horizontal flow column. The input material such as DDGS is introduced in a first direction of flow and is acted upon by an airstream force at an angle such as orthogonal to the first direction.

EXAMPLE 5

Enhanced DDGS from Elutriation Only

Enhanced DDGS is produced in the form of DDGS residue using the elutriation process as described herein. In this example, it is not necessary to add to the DDGS residue the smaller particle size subfraction resulting from a sieving step.

EXAMPLE 6

Use of DDG as Input Material

Embodiments of the invention are also applicable when DDG is used as the input material. Enhanced DDG is produced in the form of DDG residue using the elutriation process as described herein. Sieving can be used to further separate the DDG lighter fraction into a larger particle size subfraction and smaller particle size subfraction. In another embodiment, it is not necessary to add to the DDG residue the smaller particle size subfraction resulting from a sieving step. Input DDG material is also used in the generation of relatively pure fiber from the combination of elutriation and sieving, where relatively pure fiber is recovered from the sieved larger particle size subfraction of the elutriated lighter fraction.

EXAMPLE 7

Classifiers

Embodiments of the present invention can use a variety of classifying systems and apparatus capable of performing separation of a material based on particle size, density, shape, and/or weight. In particular, a gravity air elutriation system or apparatus is used. In embodiments, an air classification system can be selected from the following types: static cyclone, cyclone classifiers, single or multi-stage dynamic classifiers, cross-flow classifiers, spiral separators, high energy dispersion classifiers, and turbine classifiers (single and multiple wheel). In an embodiment, the system is an aspirator. An air classification system can be selected and adapted based on one or more properties of the input material. In an embodiment, a unit can depend on elutriation or centrifugal force or both. See C. C. Huang, 1996. In an embodiment, a unit can use a fluid other than air. In an embodiment, a fluid is nitrogen, steam, or water.

EXAMPLE 8

Fiber from Processed Corn Products

Fiber removed or harvested from processes and devices of the invention is used or further characterized. Upon processing DDGS by the combination of classifying and sieving, a relatively pure fiber fraction is obtained. This corn fiber can be used to produce corn fiber gum and corn fiber oil. The corn fiber contains phytosterols which are known to have cholesterol-reducing properties. The fiber generated from the present invention can be used as a nutraceutical. Fiber generated from the present invention can be used as a laxative. Fiber made from the present invention can optionally be further processed such as by size fractionation or fractionation based on other properties.

Fiber generated from the invention can be used for power generation by combustion. Combustion, whether or not used in power generation, can produce fiber ash which can be used in the making of cement and other composites. Fiber ash can be used in producing soaps. Fiber from the invention can be used in producing textiles and paper products.

EXAMPLE 9

Figure 14:
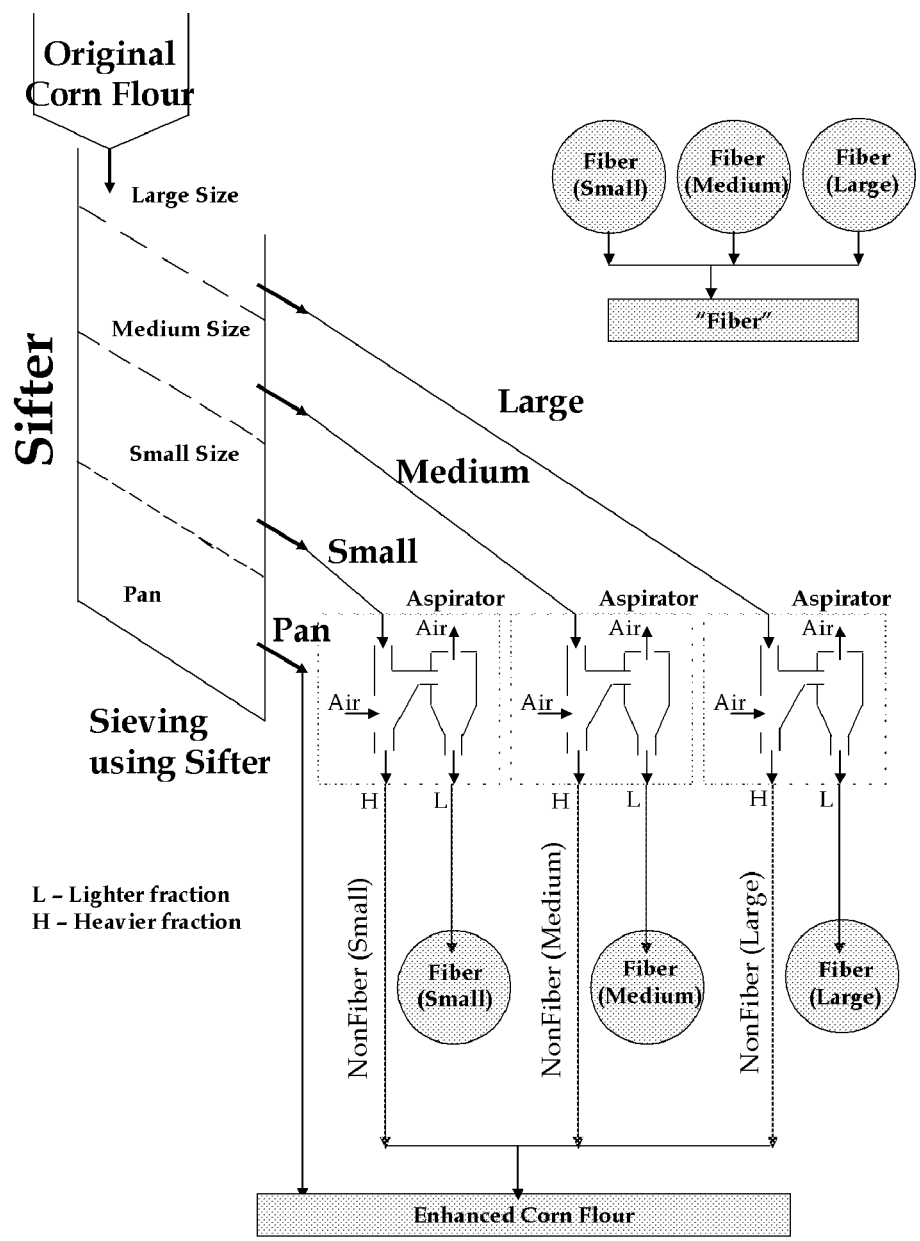
FIG. 14. Schematic of Elusieve processing for ground corn flour.

The Elusieve process, a combination of sieving and elutriation (air classification), is effective in fiber separation from ground corn flour (Srinivasan and Singh 2008a). The remaining flour (enhanced corn flour) was fermented to produce fuel ethanol. In the Elusieve process, corn flour is sieved into four size fractions: large, medium, small and pan (FIG. 14). The three biggest size fractions are air classified (aspirated) individually to separate fiber from each of the three size fractions. In aspiration, the material carried by air is called the lighter fraction, and the material not carried by air is called the heavier fraction. The operating parameter used for controlling air classification is the wt % (yield) of the lighter fraction obtained from the size fraction, which is adjusted by changing the air flowrate. Srinivasan and Singh (2008a) did not evaluate the effect of operating parameters on Elusieve processing of corn flour. The first objective of this study was to determine the effect of processing parameters (lighter fraction yields from air classification) on compositions of fractions and products. Srinivasan and Singh (2008a) measured neutral detergent fiber (NDF) and starch contents of products, not fractions. The second objective of this study was to analyze the compositions, including protein, fat and ash contents, of individual fractions.

Fiber separation from ground corn flour could also have important implications in feeding non-ruminant animals (swine and poultry). Elusieve process and other combinations of sieving and air classification were effective in separating fiber from distillers dried grains with solubles (DDGS) (Liu 2009; Srinivasan et al 2005). Fiber separation from DDGS increases its nutritional value for poultry and swine diets. In Elusieve processing of DDGS, it was envisaged that it could be beneficial to produce two DDGS products (Pan DDGS and Big DDGS) instead of just one product (enhanced DDGS). Feeding experiments with precision-fed rooster assay using cecectomized roosters showed that Pan DDGS had 7% higher true metabolizable energy ($TME_n$) than conventional DDGS (Kim et al 2010). Feeding studies on broilers at 8% DDGS inclusion levels showed that birds fed with Pan DDGS had significant difference in body weight (BW) (p=0.08) compared to birds fed with conventional DDGS and there was no significant difference in BW for birds fed with conventional and Big DDGS (Loar et al 2008). Feeding studies on growing and finishing pigs showed that enhanced DDGS from Elusieve processing increased energy concentration in DDGS by approximately 200 kCal/kg (Soares 2009).

Ground corn flour is a major ingredient in diets for swine and poultry, which do not digest fiber very well. Fiber separation could increase the digestible energy of corn flour and, thus, increase value of corn flour as an ingredient in non-ruminant diets. The third objective of this study was to carry out poultry feeding studies to determine the effect of fiber separation from corn flour on nutritional value of poultry diets. The separated fiber could be used as combustion fuel, dietary fiber ingredient in food, and for production of valuable products like cellulosic ethanol, corn fiber gum, phytosterols, oligosaccharides and polyols (Buhner and Agblevor 2004; Crittenden and Playne 1996; Dien et al 1997; Doner et al 1998; Moreau et al 1996).

Materials and Methods

Experimental Procedure for Determining Effect of Operating Parameters on Compositions of Fractions Ground corn flour was obtained from the local co-op (Oktibbeha County Co-op, Starkville, Miss.). Nearly 25 kg of ground corn flour was sieved into four different sizes using three different sized mesh screens (1,184 μm, 868 μm and 470 μm openings) in a vibratory sifter (Model LS18S33333P1WC, Sweco, Ky., USA) (FIG. 14). Only one screen was used at a time in the sifter and material was sieved at the rate of 30 minutes for every 1 kg. Samples were collected in three replicates from each size fraction for compositional analysis.

Air classification of the three largest sizes was carried out using an aspirator device (Model VJ8X6, Kice, Wichita, US) (FIG. 14). Material carried by air is called "lighter" fraction and material not carried by air is called "heavier" fraction. The smallest size fraction (pan) was not air classified because it had low fiber content. Air classification was studied at three different lighter fraction yields; 5, 10 and 15 wt %. Lighter fraction yield was controlled by adjusting the butterfly valve in the air outlet pipe of the aspirator using a trial and error method. Starting material for each air classification was 500 g, and air classification was carried out in three replicates for each size fraction at each lighter fraction yield, resulting in 18 samples (lighter as well as heavier fractions) from each size fraction. Thus, there were 3 samples from unprocessed corn flour, 12 samples from size fractions and 54 samples from air classification. There were a total of 69 samples.

The lighter fractions from each size fraction are combined to form the "fiber" product. The heavier fractions from each size fraction and the pan size fraction are combined together to form the "enhanced corn flour" product.

Experimental Procedure for Broiler Feeding Trials

Ground corn flour was procured from the local co-op (Oktibbeha County Co-op, Starkville, Miss.). In contrast to the batch operations used in sieving, as well as aspiration for determining the effect of operating parameters, the processing of corn flour for broiler feeding was carried out in the Elusieve pilot plant in a continuous operation (see Example 11). Nearly 300 kg of the ground corn flour was sieved in the Elusieve pilot plant at Pace-Seed Lab, Mississippi State University, using a rectangular rotary sifter (Srinivasan et al 2009). The sifter consisted of three decks, to produce four size fractions. The screens used were 16M (1,184 µm), 24M (868 µm) and 40M (470 µm) (FIG. 14). The large, medium, small and pan size fractions comprised 28.1, 20.9, 31.1 and 19.9 wt % of the original corn flour, respectively. The three size fractions, large, medium and small were air classified using multi-aspirators (Model VJ8X6, Kice, Wichita, Kans.) to separate out 6 to 8 wt % of each size fraction as lighter fraction (FIG. 14). The wt % of material separated as fiber product was 5.0% of the original corn flour. The compositions of regular and enhanced corn flour are listed in Table 1. Enhanced corn flour had 3.0% higher starch content than regular corn flour.

TABLE 1

Compositions (% wet basis) of regular and enhanced corn flours used in broiler feeding trials

|  | Ash | Crude Fat | Crude Protein | Neutral Detergent Fiber (NDF) | Total Starch | Moisture | Ca[1] | P[1] | $TME_n$[2] (kCal/g DM) |
|---|---|---|---|---|---|---|---|---|---|
| Enhanced Corn Flour | 1.9a | 2.9a | 7.9a | 7.6b | 63.8a | 13.3a | 0.11 | 0.30 | 3.810 |
| Regular Corn Flour | 1.4b | 2.6a | 7.8a | 8.6a | 60.8b | 13.8a | 0.06 | 0.30 | 3.854 |

[1]Analyzed in duplicate
[2]$TME_n$ - True Metabolizable Energy; values are the observed means of four replicates; measured at University of Illinois' research facility using cecectomized roosters.

Values are means of 6 replicates; coefficients of variation were less than 7%; within a column, values followed by the same letter are not different ($p<0.05$).

Most procedures used in this broiler feeding trial were similar to those used by Loar et al (2009). This grow-out study encompassed the period between 0 to 21 d of age using Ross×Ross 308 males obtained from a commercial hatchery. Day-old chicks were randomly placed in each of 24 floor pens (15 birds/pen; 360 birds total) at a density of 0.09 m²/bird. The experimental house was close-sided and had thermostatically controlled heating, cool cells and cross-ventilation. Each pen had built-up litter, a hanging feeder (22.5 kg capacity) and a water line (3 nipples/pen). The lighting program was 23 h light and 1 h dark, and ventilation was accomplished by negative air pressure. Chicks were vaccinated for Marek's disease (via in ovo administration at d 18), Newcastle disease and infectious bronchitis (via coarse spray at hatch).

There were 2 different dietary treatments (regular corn diet and enhanced corn diet) with each treatment being replicated 12 times. Proximate analysis was performed on the experimental diets, and values are reflected in Table 2. The $TME_n$ values for regular corn flour were 3.854 and 3.810 kCal/kg, respectively (Table 1). True digestibility coefficients of amino acids were determined for corn via the use of precision-fed cecectomized roosters (Table 3). The values obtained for $TME_n$ and amino acid digestibility were incorporated in the feed formulation linear programming software matrix, and diets were then formulated to be isocaloric, isonitrogenous, and similar in calcium, phosphorus and all limiting amino acids. Diets met or exceeded current recommendations for nutrients, and feed and water was provided on an ad libitum basis (NRC 1994).

TABLE 2

Composition of experimental diets (% wet basis)

|  | Regular corn | Enhanced corn |
|---|---|---|
| Ingredients |  |  |
| Corn | 55.818 | 55.016 |
| Soybean meal | 38.141 | 38.397 |
| Poultry fat | 2.353 | 2.979 |
| Calcium carbonate | 1.434 | 1.356 |
| Dicalcium phosphate | 1.115 | 1.125 |
| Sodium chloride | 0.455 | 0.462 |
| DL-Methionine | 0.293 | 0.283 |

TABLE 2-continued

Composition of experimental diets (% wet basis)

|  | Regular corn | Enhanced corn |
|---|---|---|
| Vitamin/mineral premix[1] | 0.25 | 0.25 |
| L-Lysine | 0.067 | 0.053 |
| Coccidiostat[2] | 0.05 | 0.05 |
| L-Threonine | 0.025 | 0.029 |
| Calculated composition |  |  |
| Crude protein, % | 23.68 | 23.78 |
| NDF, % | 7.20 | 6.60 |
| $TME_n$, kcal/kg | 3,300 | 3,300 |
| Calcium, % | 0.90 | 0.90 |
| Available phosphorus, % | 0.45 | 0.45 |
| Lysine, % digestible | 1.22 | 1.22 |
| TSAA, % digestible | 0.91 | 0.91 |
| Threonine, % digestible | 0.79 | 0.79 |
| Sodium, % | 0.22 | 0.22 |
| Diet cost, $/metric tonne | 279.50 | 282.20 |

[1]The vitamin and mineral premix contained per kg of diet: retinyl acetate, 2,654 µg; cholecalciferol, 110 µg; dl-α-tocopherol acetate, 9.9 mg; menadione, 0.9 mg; $B_{12}$, 0.01 mg; folic acid, 0.6 µg; choline, 379 mg; d-pantothenic acid, 8.8 mg; riboflavin, 5.0 mg; niacin, 33 mg; thiamin, 1.0 mg; d-biotin, 0.1 mg; pyridoxine, 0.9 mg; ethoxiquin, 28 mg; manganese, 55 mg; zinc, 50 mg; iron, 28 mg; copper, 4 mg; iodine, 0.5 mg; selenium, 0.3 mg.
[2]Dietary inclusion of 60 g salinomycin sodium per 907.2 kg of feed.

TABLE 3

True digestibility coefficients of major amino acids for regular and enhanced corn flour determined by precision feeding to cecectomized roosters.

| Amino Acid | Thr | Cys | Val | Met | Ile | Leu | Lys | Arg | Trp |
|---|---|---|---|---|---|---|---|---|---|
| Regular Corn Flour | 86.9 (11.2) | 88.4 (12.4) | 83.2 (6.4) | 83.4 (4.9) | 81.9 (6.6) | 90.8 (4.5) | 71.0 (7.4) | 86.1 (7.3) | 94.1 (5.6) |
| Enhanced Corn Flour | 75.5 (10.3) | 75.2 (10.2) | 77.6 (2.4) | 84.7 (1.2) | 77.4 (2.1) | 88.3 (1.6) | 62.4 (10.0) | 82.4 (2.9) | 86.0 (8.2) |

(Values are means from four replicates. Values in parentheses are standard deviations.)

All birds in each pen were weighed collectively at the beginning and at the end of the study. Feed consumption and mortality were monitored throughout the study, and feed conversion was corrected for mortality, and represents grams of feed consumed by all birds in a pen divided by grams of body weight gain per pen. All procedures were approved by the Mississippi State University's Institutional Animal Care and Use Committee.

Compositional Analysis

Samples were analyzed for crude protein (AOAC 2003, Method: 990.03), crude fat (AOAC 2003, Method: 920.39) and ash (AOAC 2003, Method: 942.05) (AOAC, 2003). NDF content was determined by boiling a 0.5 g sample in 100 ml of neutral detergent (ND) and 50 µl of heat stable amylase (Van Soest et al., 1991). Moisture content was determined using two-stage convention oven method (Approved Method 44-18, AACC International 2000) (AACC International 2000). Starch content was determined using the glucoamylase procedure (AACC International 2000) (Method 77-11). Analyses were carried out at a commercial laboratory (Midwest Labs, Omaha, Nebr.). Coefficients of variation (CV) for compositions were less than 10%, except for starch and NDF, which had CV less than 15%.

NDF Separation Factor

The NDF separation factor indicates the selectivity of air in carrying fiber rather than non-fiber components at the operating air velocity (Srinivasan et al 2005). A high NDF separation factor indicates that the selectivity of air in carrying fiber is high. The NDF separation factor for aspiration is defined as the ratio of the NDF %/Non-NDF % of the lighter fraction to the NDF %/Non-NDF % of the heavier fraction (Srinivasan et al 2005). It is calculated as:

[NDF %/(100 NDF %)]$_{Lighter\ fraction}$/[NDF %/(100−NDF %)]$_{Heavier\ fraction}$.

Statistical Analyses

Data in this experiment were evaluated using analyses of variance in a randomized complete block design with one pen representing an experimental unit. Percentage data for mortality were transformed to arcsine for analysis. All data were analyzed by the GLM procedure of SAS (2004), and treatment effects were separated using Tukey's multiple comparisons test option of SAS (2004) using an α of 0.05.

Results and Discussion

Effect of Operating Parameters on Compositions of Fractions

Pan size fraction comprised 28.1 wt % of corn flour and had the highest starch content (75.4%) (Table 4). Pan size fraction had lower NDF (5.4%) compared to the unprocessed corn flour (9.9%) and had higher starch content (75.4%) compared to unprocessed corn flour (71.7%). The three biggest size fractions had higher NDF and lower starch contents than unprocessed corn flour (Table 4).

TABLE 4

Wt % and compositions of size fractions (% db) obtained by sieving of ground corn flour.

| Material | Wt % | NDF | Starch | Crude Protein | Crude Fat | Ash |
|---|---|---|---|---|---|---|
| Unprocessed Corn Flour | 100.0 | 9.9b | 71.7b | 9.0a | 4.4a | 1.5a |
| 16M (>1,184 µm) | 31.1 | 11.7a | 67.7c | 9.2a | 4.0a | 1.6a |
| 24M (868 to 1,184 µm) | 16.7 | 11.9a | 67.5c | 9.8a | 4.0a | 1.4a |
| 40M (470 to 868 µm) | 24.1 | 11.6a | 66.9c | 9.4a | 3.9a | 1.3a |
| Pan (<470 µm) | 28.1 | 5.4c | 75.4a | 8.3ab | 4.1a | 1.3a |

(NDF - neutral detergent fiber; values are means of three replicates; within a column, values followed by the same letter are not different (p < 0.05).)

Within each size fraction, lighter fractions had higher NDF and lower starch contents compared to heavier fractions (Table 5). In other words, the lighter fractions were more enriched in fiber, which was also reflected in the high NDF separation factors (>7.5). Protein and fat contents of lighter fractions were lower or same compared to corresponding heavier fractions (Table 5). As lighter fraction yield was increased within each size fraction, there was a decrease in NDF content, a decrease in NDF separation factor and an increase in starch, protein and fat contents of lighter fractions due to increased carry over of nonfiber particles, along with fiber at higher air velocities. For example, as lighter fraction yield was increased from 3.8 to 11.6%, the NDF of lighter fraction decreased from 61.9 to 45.6%, NDF separation factor decreased from 24.6 to 19.8%, starch content of lighter fraction increased from 25.2 to 33.7%, protein content of lighter fraction increased from 5.9 to 9.4% and fat content of lighter fraction increased from 2.1 to 4.0% (Table 5). Similar trends were observed for NDF, protein and fat contents in air classification of DDGS size fractions (Srinivasan et al 2008; Srinivasan et al 2005). As lighter fraction yield was increased within each size fraction, there was a decrease in NDF content and an increase in starch contents of heavier fractions due to increased removal of fiber from the size fractions (Table 5). For example, as lighter fraction yield was increased from 7.4 to 12.6%, the NDF of heavier fraction decreased from 8.7 to 6.8% and starch content of heavier fraction increased from 73.6 to 75.1% (Table 5).

TABLE 5

Compositions (% db) and yields of fractions obtained by air classification of size fractions at 5, 10 and 15% lighter fraction yields.

| Size Fraction | Lighter Fraction Yield % | NDF L | NDF H | Separation Factor | Starch L | Starch H | Crude Protein L | Crude Protein H | Crude Fat L | Crude Fat H | Ash L | Ash H |
|---|---|---|---|---|---|---|---|---|---|---|---|---|
| 16M (>1,184 µm) | 3.8 | 61.9a | 6.2d | 24.6 | 25.2e | 72.0b | 5.9b | 9.3a | 2.1b | 3.1a | 1.3 | 1.3 |
|  | 11.6 | 45.6b | 4.1e | 19.8 | 33.7d | 76.6a | 9.4a | 9.4a | 4.0a | 3.3a | 1.9 | 1.3 |
|  | 15.3 | 40.3c | 3.9e | 16.5 | 40.5c | 77.3a | 9.6a | 9.3a | 4.5a | 3.5a | 2.0 | 1.3 |
| 24M (868 to 1,184 µm) | 5.6 | 56.0a | 7.3c | 16.1 | 30.4e | 72.5b | 6.5c | 10.0a | 2.4b | 3.8a | 1.6 | 1.5 |
|  | 11.7 | 56.3a | 4.8d | 25.6 | 27.5d | 75.8a | 7.1bc | 10.1a | 2.7b | 3.4a | 1.4 | 1.4 |
|  | 19.1 | 41.5b | 4.1e | 16.5 | 38.1c | 75.3a | 9.1ab | 9.9a | 4.4a | 3.8a | 2.0 | 1.5 |
| 40M (470 to 868 µm) | 7.4 | 41.8a | 8.7d | 7.5 | 38.2d | 73.6b | 8.2b | 9.4a | 4.7a | 4.0a | 1.9 | 1.2 |
|  | 12.6 | 39.4b | 6.8e | 8.9 | 41.0c | 75.1a | 9.2a | 9.4a | 5.0a | 4.2a | 2.0 | 1.2 |
|  | 20.1 | 36.3c | 6.0e | 9.0 | 42.9c | 76.3a | 9.3a | 9.4a | 5.1a | 4.3a | 1.8 | 1.3 |

(L - lighter fraction, H - heavier fraction, NDF - neutral detergent fiber; values are means of three replicates; within each size fraction, values followed by the same letter are not different ($p < 0.05$))

NDF separation factors were higher for aspiration of size fractions from ground corn flour (7.5 to 25.6) compared to DDGS (1.2 to 4.3), though the NDF content of lighter fractions from DDGS and ground corn flour were similar, because heavier fractions had lower NDF for ground corn flour (3.9 to 8.7%) compared to DDGS (24.2 to 37.8%) (Table 5; Srinivasan et al 2008; Srinivasan et al 2005). Heavier fractions from ground corn flour had lower NDF compared to heavier fractions from DDGS because NDF of unprocessed ground corn flour (9.9%) itself was lower than NDF of unprocessed DDGS (28.0 to 33.6%) (Table 4; Srinivasan et al 2008; Srinivasan et al 2005).

The working principle for fiber separation from DDGS was determined in a detailed study by Srinivasan and Singh (2008b). Fiber particles were selectively carried by air because fiber particles had lower weight compared to non-fiber particles, despite having higher particle density, due to flat shape of fiber particles. Flat shape of fiber particles aided in their being selectively carried by air also because flat particles experience higher drag force compared to spherical particles. It is expected that working principle of fiber separation from ground corn flour could be similar to that for DDGS. As the size fractions became smaller in size, the NDF separation factors decreased (Table 5). For example, as size decreased from 16M (>1,184 µm) to 40M (470 to 868 µm), the NDF separation factors decreased from a range of 16.5-24.6 to a range of 7.5-9.0 (Table 5). The decrease in separation effectiveness as size decreased could be because flat shaped particles of small size fractions tend to behave like near-spherical particles as thickness of smaller flat particles is closer to the length of the other dimensions; hence, the difference in properties of fiber and non-fiber gets narrowed down for smaller size fractions.

At lighter fraction yields of 5%, the fiber separated was 3.9 wt % of the original corn flour. At low lighter fraction yield (5%), the loss of starch into fiber was lower (1.9%) and at higher lighter fraction yield (15%), the loss of starch into fiber was higher (7.4%) (Table 6). Elusieve processing, in batch operation, increased starch content of corn flour by 4.4 to 4.8% and decreased NDF of corn flour by 1.3 to 1.5%. There was no substantial effect of lighter fraction yields on starch or NDF contents of corn flour and, hence, it would be best to operate at lighter fraction yields of 5% to minimize on the loss of starch (Table 6). As lighter fraction yield increased, the fiber product's NDF content decreased, and starch content increased, signifying that the fiber product's purity was lower at higher lighter fraction yields.

TABLE 6

Compositions (% wb) and wt % of products obtained by Elusieve processing of ground corn flour at 5, 10 and 15% lighter fraction yields.

| Product | Lighter Fraction Yield | Wt % | NDF | Starch | Protein | Fat | Ash | % Loss of Starch in Fiber Product |
|---|---|---|---|---|---|---|---|---|
| Unprocessed Corn Flour | — | 100.0 | 8.5 | 61.4 | 7.7 | 3.8 | 1.3 | — |
| Enhanced Corn Flour | 5% | 96.1 | 7.0 | 65.8 | 7.9 | 3.1 | 1.1 | — |
|  | 10% | 91.4 | 7.2 | 66.2 | 8.0 | 3.3 | 1.1 | — |
|  | 15% | 87.2 | 7.0 | 66.0 | 7.9 | 3.4 | 1.2 | — |
| Fiber | 5% | 3.9 | 42.4 | 30.2 | 7.4 | 3.2 | 1.6 | 1.9 |
|  | 10% | 8.6 | 40.2 | 30.6 | 7.7 | 3.6 | 1.6 | 4.3 |
|  | 15% | 12.8 | 33.9 | 35.4 | 8.1 | 4.1 | 1.7 | 7.4 |

(NDF - neutral detergent fiber; values are calculated from Tables 4 and 5)

Broiler Feeding Trials

Enhanced corn flour had 3.0% higher starch content than regular corn flour (Table 1). Continuous Elusieve operation for broiler feeding trials resulted in smaller increase in starch content of corn flour (by 3.0%) compared to batch operation (by 4.4 to 4.8%) used in studying effect of operating parameters, perhaps, because of inefficiencies in continuous sieving operation that result in retention of oversized/undersized material in size fractions. There was a significant increase in body weight gain for the treatment that had enhanced corn flour compared to the treatment that had regular corn flour as the ingredient (Table 7). The increase in body weight gain was 4.3% compared to the regular corn flour diet. The feed conversion ratio was significantly lower (by 3 points) for the enhanced corn diets compared to the regular corn diets.

TABLE 7

Performance of broiler chicks fed various corn sources

| Treatment | BW gain (g/bird) | Feed intake (g/bird) | Feed conversion[1] | Mortality (%) |
|---|---|---|---|---|
| Regular corn | 825.7[b] | 1,169 | 1.419[a] | 2.2 |
| Enhanced corn | 861.0[a] | 1,197 | 1.390[b] | 1.7 |
| SEM | 8.3 | 11.1 | 0.0064 | 1.10 |
| Treatment P value | 0.0065 | 0.09 | 0.006 | 0.73 |

BW - Body weight
[a-b]Means not followed by the same letter within a column differ significantly (p < 0.05). Observed means for BW gain, feed conversion, feed intake, and mortality are based on 12 replicate pens per treatment.
[1]Values represent the feed conversion ratio after being adjusted for mortality weight.

Conclusions

Fiber separation increased starch content in corn flour by 3.0 to 4.8%. Least loss of starch into fiber product was achieved at 5% lighter fraction yields. Loss of starch was higher as lighter fraction yields increased. The body weight gain of chicks (21 d study) was higher by 4.3%, and feed conversion ratio was lower, when fed with diets incorporating enhanced corn flour, compared with diets incorporating regular corn flour. This demonstrates the increased nutritional value to broilers from fiber separation. Thus, incorporation of fiber separation from corn flour in poultry feed mills could be helpful in increasing revenues from poultry farming.

EXAMPLE 10

Other Agricultural Products as Input Material

Embodiments of the invention are also applicable when other input materials are used. For example, another input material can be legumes (e.g. soybeans), barley, sorghum, wheat, or a product of each derived therefrom, respectively. In each case, process and device parameters are optimized regarding the physical properties of the input material. For example, an air velocity rate is optimized for elutriation of a sorghum product. Similarly, sieving parameters are optimized for sieving a sorghum product. Analogous customizations are made for a wheat product. For example, a sorghum or wheat product can be a processed product similar to DDGS produced from corn as the grain starting material.

A processed sorghum product is used as an input material. The input material is separated by particle size using a sieve parameter so as to effect separation of a larger particle size fraction and a smaller particle size fraction. The larger fraction, smaller fraction, or both larger and smaller fractions are then subjected to classification so as to effect separation of one or more fiber-enriched lighter fractions and one or more fiber-reduced heavier fractions.

A processed wheat product is used as an input material. The input material is separated by particle size using a sieve parameter so as to effect separation of a larger particle size fraction and a smaller particle size fraction. The larger fraction, smaller fraction, or both larger and smaller fractions are then subjected to classification so as to effect separation of one or more fiber-enriched lighter fractions and one or more fiber-reduced heavier fractions.

EXAMPLE 11

Materials and Methods

Commercial SBM, WM and CSM were procured from a local co-op store (Oktibbeha county Coop, Starkville, Miss., USA). A vibro-energy sifter (Sweco, Model LS18S33333P1WC, KY, USA) was used for sieving. The screens used were 10M (1,885 µm), 12M (1,532 µm), 14M (1,295 µm), 16M (1,130 µm), 18M (980 µm), 20M (864 µm), 24M (704 µm), 30M (516 µm), 35M (447 µm), 40M (381 µm), 50M (279 µm) and 60M (234 µm). The letter 'M' in screen labels refers to market grade cloth.

Air classification of size fractions was performed using a multi-aspirator system (Model VJ8X6, Kice, Wichita, US). The multi-aspirator has a feeding section or a feeder through which the size fraction was fed, a source of suction (centrifugal fan) with damper control, connecting duct and a cyclone receiver/separator. The multi-aspirator has a series of 4 or 6 slides running parallel to the section through which the lighter size fraction which qualify to be lifted were carried away by the suction air from centrifugal fan and collected at the outlet of receiver, and the heavier fraction with lighter fraction slides down the feeding section into a collection drum. In this study, the heavier fractions were manually fed twice into the aspirator to ensure thoroughness of aspiration.

Experimental Procedure

Figure 15:
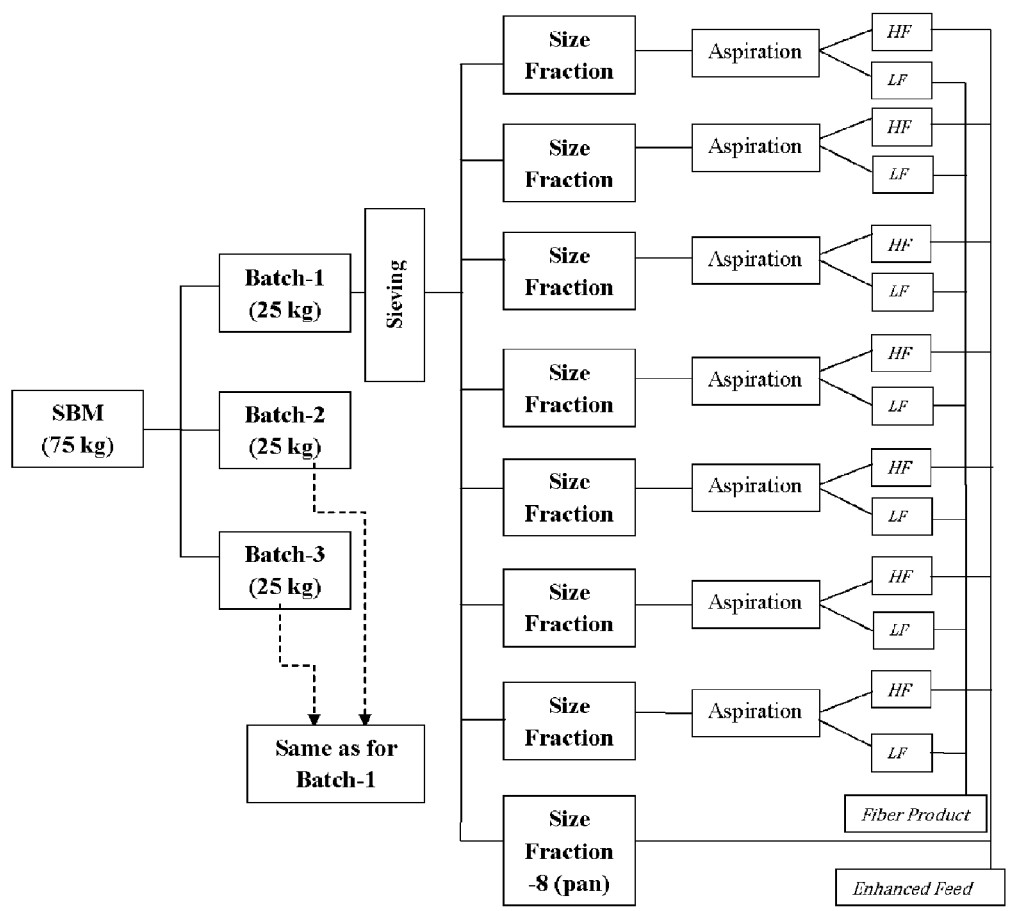
FIG. 15 shows an Experimental scheme for sieving and air classification of three batches of feeds of SBM.

About 75 kg of SBM was divided into three batches of 25 kg each (batch-1, batch-2 and batch-3) (FIG. 15). Each batch of SBM was sieved into 8 different size fractions sieving in a vibro-energy separator using 7 different screens. For screening of material, only one screen was used in the sifter; screens were not stacked in the sifter. Material passed through the screen of the largest openings; the material on the top was named as size fraction-1. The through was collected and fed to the sifter after replacing it with next biggest screen. Likewise, the through material was sieved using each of the 7 screens, and the last was named as pan. The material obtained in pan was not subjected to air classification. The screens were chosen such that each size fraction comprised nearly 10% (by weight) of the whole material. The same procedure was repeated for CSM and WM also, except that only 6 screens were used for CSM and WM instead of 7 screens used for SBM.

For SBM, all size fractions, except for the pan, were air classified in a multi-aspirator for two different yields (5% and 15%) of lighter fraction. The yield of lighter fraction was adjusted by controlling the damper in the multi-aspirator. For CSM, all size fractions except for the largest and pan size fractions were air classified. For CSM, the largest size fraction was not air classified because no lighter fraction was obtained by air classification. For WM, all size fractions, except for the pan, were air classified. Samples of lighter and heavier fractions from each size fraction were finely ground in a grinder (Model CBG100W, Black and Decker, Towson, Md., USA) and analyzed in a commercial lab (Midwest Labs, Nebraska, US) for neutral detergent fiber (NDF), protein, ash and moisture contents. NDF procedure used in this study is aNDF-NDF assayed with a heat stable amylase and expressed inclusive of residual ash.

Analytical Tests

Samples were analyzed for crude protein (AOAC 2003, Method: 990.03), crude fat (AOAC 2003, Method: 920.39) and ash (AOAC 2003, Method: 942.05) (AOAC, 2003). NDF (aNDF—NDF assayed with a heat stable amylase and expressed inclusive of residual ash) content was determined by boiling a 0.5 g sample in 100 ml of neutral detergent (ND) and 50 µl of heat stable amylase (Van Soest et al., 1991). The sample is incubated overnight with amylase at highest possible temperature to avoid degradation of hemicellulosic components in the feed (Van Soest et al., 1991). Moisture content was determined using two-stage convention oven method (Approved Method 44-18, AACC International 2000) (AACC, 2000).

NDF Separation Factor

The ratio of NDF % to non-NDF % of the lighter fraction to the NDF % to non-NDF % of the heavier fraction is defined as NDF separation factor (Srinivasan et al., 2005) and calculated as:

$$\alpha_{NSF} = [NDF\%/(100-NDF\%)]_{Lighter\ fraction} / [NDF\%/(100-NDF\%)]_{Heavier\ fraction}.$$

NDF separation factor is an indicator of the effectiveness of separation of fiber from the non-fiber fractions. Higher NDF separation factor signifies a better fiber separation.

Statistical Analysis

All the experiments were conducted in three replicates. Three batches of the enhanced SBM, CSM and WM were obtained by sieving and air classification. Means of NDF, protein, fat and ash were compared by ANOVA analysis (SAS Institute, Cary, N.C.) at statistical significance level of 5% ($P<0.05$).

Results

The compositions of fractions are reported in dry basis, while the compositions of products and unprocessed animal feeds are reported in wet basis. The compositions of products and unprocessed material are reported in wet basis because feeds are usually sold based on wet basis composition. The moisture content of the wet animal feeds is around 11 to 13%. The composition of animal feeds is shown in Table 8. SBM has much lower NDF than the CSM and WM samples. SBM had the highest protein content (53.9%) of all the animal feeds chosen for the study followed by CSM (49.9%), and the lowest was WM (19.2%).

TABLE 8

Characteristics of unprocessed animal feed samples (% wb)

| Feed | NDF | Protein | Fat | Ash | Moisture |
|------|------|---------|-----|-----|----------|
| SBM  | 7.2  | 47.7    | 1.1 | 6.0 | 11.6     |
| CSM  | 19.9 | 43.9    | 4.3 | 7.0 | 12.1     |
| WM   | 34.7 | 16.9    | 2.8 | 4.2 | 12.3     |

(NDF - Neutral Detergent Fiber.)

Soybean Meal

Table 9 shows the SBM composition and wt % of size fractions obtained after sieving. The amounts of material (Wt %) in the eight size fractions 10M, 12M, 16M, 20M, 24M, 30M, 40M and pan were 21.0, 9.1, 13.5, 10.4, 9.6, 8.7, 9.8 and 18.1% respectively (Table 9). There was no substantial difference in compositions of size fractions (Table 9).

FIG. 15 shows a process used for sieving and air classification of three batches of feeds for SBM. LF=Lighter Fraction, HF=Heavier Fraction. Batch-2 & Batch-3 are also sieved and air classified like Batch-1. Experimental scheme for CSM and WM were similar to SBM, except: 1) only 7 size fractions were produced instead of 8 size fractions for SBM 2) for CSM, largest size fraction was not aspirated.

TABLE 9

Composition and Wt % of fractions obtained by sieving SBM (% db)

| Size | Wt | NDF | Protein | Fat | Ash |
|------|-----|------|---------|-----|-----|
| Unprocessed* | 100.0 | 8.1 | 53.9 | 1.3 | 6.8 |
| 10M (>1,885 μm) | 21.0 | 7.0$^b$ | 55.8$^a$ | 1.6$^a$ | 6.7$^c$ |
| 12M (1,532 to 1,885 μm) | 9.1 | 8.0$^b$ | 55.9$^a$ | 1.1$^b$ | 6.5$^c$ |
| 16M (1,130 to 1,532 μm) | 13.5 | 8.1$^{a,b}$ | 55.0$^a$ | 1.0$^b$ | 6.6$^c$ |
| 20M (864 to 1,130 μm) | 10.4 | 7.7$^b$ | 55.0$^a$ | 1.0$^b$ | 6.7$^c$ |
| 24M (704 to 864 μm) | 9.6 | 7.9$^b$ | 55.3$^a$ | 1.0$^b$ | 6.8$^{b,c}$ |
| 30M (542 to 704 μm) | 8.7 | 11.4$^a$ | 54.9$^a$ | 1.2*b | 6.8$^{b,c}$ |
| 40M (381 to 542 μm) | 9.8 | 9.6$^{a,b}$ | 54.7$^a$ | 1.0$^b$ | 7.1*$^b$ |
| Pan (<381 μm) | 18.1 | 10.6$^{a,b}$ | 51.1$^b$ | 1.3*$^{a,b}$ | 6.8$^a$ |

(NDF - Neutral Detergent Fiber, L - lighter fraction, H - heavier fraction. Composition values within each column and having same superscripted letter are not different. The COVs were less than 15% for NDF, Protein, Fat and Ash.
*indicates those fractions whose COVs were greater than 15%.
Unprocessed* SBM compositions were from one sample (not three samples).)

Air classification of SBM size fractions was effective in separating fiber as indicated by higher NDF in lighter fractions compared to the corresponding heavier fractions and the unprocessed SBM (Table 10). For the 10M size fraction, the NDF increased from 7.0% in unprocessed SBM to 49.2% in the lighter fraction at lower yield (5.0%) and 18.8% at higher yield (10.8%) of lighter fraction (Table 10). The moisture content of the heavier fraction varied from 10.7 to 11.7% and that of lighter fraction varied from 10.3 to 11.6%.

TABLE 10

Composition and Wt % of fractions obtained by air classification of SBM size fractions

| Size | Lighter fraction Yield (Wt %) | NDF L | NDF H | Separation Factor | Protein L | Protein H | Fat L | Fat H | Ash L | Ash H |
|------|------|------|------|------|------|------|------|------|------|------|
| 10 M (>1,885 μm) | 0.0 | — | 7.0$^{b,c}$ | — | — | 55.8$^a$ | — | 1.6$^a$ | — | 6.7$^a$ |
|  | 5.0 | 49.2*$^a$ | 5.5$^c$ | 16.6 | 25.2*$^c$ | 56.3$^a$ | 0.5*$^b$ | 0.9$^{a,b}$ | 5.5*$^b$ | 6.8$^a$ |
|  | 10.8 | 18.8$^b$ | 7.1$^{b,c}$ | 3.0 | 45.7$^b$ | 56.9$^a$ | 0.9*$^b$ | 1.0$^{a,b}$ | 5.8$^b$ | 7.0$^a$ |
| 12 M (1,532 to 1,885 μm) | 0.0 | — | 8.0$^c$ | — | — | 55.9$^a$ | — | 1.1$^a$ | — | 6.5$^b$ |
|  | 3.6 | 63.2$^a$ | 5.4$^c$ | 29.9 | 14.2$^c$ | 55.9$^a$ | 0.2*$^d$ | 0.8$^b$ | 5.1$^d$ | 6.8$^{a,b}$ |
|  | 9.7 | 25.4$^b$ | 5.3$^c$ | 6.1 | 43.0$^b$ | 57.1$^a$ | 1.0$^b$ | 0.9$^b$ | 6.2$^a$ | 6.8$^a$ |
| 16 M (1,130 to | 0.0 | — | 8.1$^c$ | — | — | 55.0$^b$ | — | 1.0$^{a,b}$ | — | 6.6$^{a,b}$ |
|  | 3.4 | 65.5$^a$ | 5.6$^d$ | 31.9 | 13.3$^d$ | 56.4$^{a,b}$ | 0.2*$^c$ | 0.8$^b$ | 5.2$^c$ | 7.6*$^a$ |

TABLE 10-continued

Composition and Wt % of fractions obtained by air classification of SBM size fractions

| Size | Lighter fraction Yield (Wt %) | NDF L | NDF H | Separation Factor | Protein L | Protein H | Fat L | Fat H | Ash L | Ash H |
|---|---|---|---|---|---|---|---|---|---|---|
| 1,532 µm) | 7.0 | 15.7$^b$ | 5.0$^d$ | 3.6 | 49.7$^c$ | 57.4$^a$ | 1.1$^a$ | 1.0$^{a,b}$ | 6.3$^b$ | 7.0$^{a,b}$ |
| 20 M | 0.0 | — | 7.7$^c$ | — | — | 55.3$^a$ | — | 1.0$^{a,b}$ | — | 6.7$^{a,b}$ |
| (864 to | 4.3 | 56.9*$^a$ | 6.6$^c$ | 18.8 | 19.4*$^c$ | 56.5$^a$ | 0.3*$^c$ | 0.8*$^b$ | 5.4*$^c$ | 6.8$^{a,b}$ |
| 1,130 µm) | 11.0 | 26.1$^b$ | 5.3$^c$ | 6.4 | 40.7$^b$ | 57.4$^a$ | 1.2*$^a$ | 0.8$^b$ | 6.4$^b$ | 7.1$^a$ |
| 24 M | 0.0 | — | 7.9$^c$ | — | — | 55.3$^a$ | — | 1.0$^a$ | — | 6.8$^b$ |
| (704 to 864 µm) | 4.9 | 59.5$^a$ | 5.9$^c$ | 23.2 | 17.9$^c$ | 56.2$^a$ | 0.2*$^b$ | 0.9$^a$ | 5.3$^d$ | 7.0$^{a,b}$ |
|  | 12.0 | 26.9*$^b$ | 5.6$^c$ | 6.2 | 42.3$^b$ | 57.6$^a$ | 1.0*$^a$ | 0.8*$^a$ | 6.3$^c$ | 7.0$^a$ |
| 30 M | 0.0 | — | 11.4$^{a,b}$ | — | — | 54.9$^{a,b}$ | — | 1.2$^a$ | — | 6.8$^a$ |
| (542 to 704 µm) | 5.9 | 28.9*$^a$ | 6.3$^b$ | 6.0 | 39.8*$^c$ | 57.1$^a$ | 1.0*$^a$ | 0.9$^a$ | 6.5*$^a$ | 6.9$^a$ |
|  | 17.4 | 26.8*$^a$ | 5.6$^b$ | 6.2 | 41.7*$^{b,c}$ | 56.8$^a$ | 0.9*$^a$ | 0.8$^a$ | 6.2*$^a$ | 6.9$^a$ |
| 40 M | 0.0 | — | 9.6$^c$ | — | — | 54.7$^a$ | — | 1.0$^{ab}$ | — | 7.1$^a$ |
| (381 to 542 µm) | 4.7 | 36.2$^a$ | 7.1*$^d$ | 7.5 | 33.0$^c$ | 55.9$^a$ | 0.9*$^b$ | 0.9$^b$ | 6.0$^c$ | 7.3$^a$ |
|  | 10.4 | 21.6$^b$ | 6.0$^d$ | 4.3 | 46.3$^b$ | 55.4$^a$ | 1.3$^a$ | 1.0$^b$ | 6.4$^b$ | 7.2$^a$ |

NDF - Neutral Detergent Fiber, L - lighter fraction, H - heavier fraction. Composition values within each size fraction and having same superscripted letter are not different. Values at 0.0% yield indicate composition of size fraction. COVs of wt % NDF, Protein, Fat and Ash were less than 15, 10, 15 and 5% respectively.
*indicates those fractions whose COVs were greater than the threshold values.

The overall fiber separation from SBM and the composition of the final products, i.e. fiber and enhanced SBM, at low yield of lighter fraction, are reported in Table 11. The compositions of fiber and enhanced SBM in Table 11 and Table 12 were calculated from Table 9 and Table 10. The combination of sieving and air classification with low yield resulted in 3.7% of fiber being separated from SBM and NDF increasing from 7.2% in unprocessed SBM to 44.7% in the fiber product (Table 11).

TABLE 11

Composition of products from processing of SBM with low lighter fraction yields (5%) in air classification (% wb).

| Product | Wt | NDF | Protein | Fat | Ash |
|---|---|---|---|---|---|
| Unprocessed SBM | 100.0 | 7.2 | 47.7 | 1.1 | 6.0 |
| Fiber | 3.7 | 44.7 | 21.5 | 0.5 | 5.0 |
| En SBM | 96.3 | 6.1 | 49.1 | 0.8 | 6.7 |

NDF - Neutral Detergent Fiber, En - Enhanced.

An increase of protein content by 1.4% in enhanced SBM and lower protein content in separated fiber indicate that combination of sieving and air-classification was effective in enhancing protein content of SBM.

Table 12 gives the cumulative composition of products from processing SBM at high yields of lighter fraction. Fiber product was of higher quantity (8.9%) at higher yield of lighter fraction compared to the low yield of lighter fraction (3.7%) but at the cost of fiber purity. Lower NDF (20.3%) in fiber indicates that more non-fiber was carried over along with fiber at high yield of lighter fraction. The protein in fiber (39.3% w/w) is also higher for high yields of lighter fraction compared to the fiber obtained at low yields of lighter fraction.

TABLE 12

Composition of products from processing of SBM with high lighter fraction yields (15%) in air classification (% wb)

| Product | Wt | NDF | Protein | Fat | Ash |
|---|---|---|---|---|---|
| Unprocessed SBM | 100.0 | 7.2 | 47.7 | 1.1 | 6.0 |
| Fiber | 8.9 | 20.3 | 39.3 | 0.9 | 5.5 |
| En SBM | 91.1 | 6.0 | 49.7 | 0.9 | 6.7 |

NDF - Neutral Detergent Fiber, En - Enhanced.

Cottonseed Meal

For CSM, it was found that sieving alone resulted in two size fractions 40M and pan that had lower NDF and higher protein contents than unprocessed CSM (Table 13).

TABLE 13

Composition and Wt % of fractions obtained by sieving cottonseed Meal (CSM) (% db)

| Size | Wt | NDF | Protein | Fat | Ash |
|---|---|---|---|---|---|
| Unprocessed | 100.0 | 22.6$^{d,e}$ | 49.9$^b$ | 4.9$^c$ | 8.0$^c$ |
| 10 M (>1,885 µm) | 21.8 | 25.1$^{c,d}$ | 46.5$^c$ | 3.2$^f$ | 7.3$^{d,e}$ |
| 12 M (1,532 to 1,885 µm) | 9.4 | 27.8$^{b,c}$ | 45.5$^{c,d}$ | 3.6$^e$ | 6.9$^f$ |
| 16 M (1,130 to 1,532 µm) | 14.1 | 31.3$^a$ | 43.9$^d$ | 3.7$^e$ | 7.2$^{d,ef}$ |
| 20 M (864 to 1,130 µm) | 10.8 | 30.2$^{a,b}$ | 46.1$^{c,d}$ | 3.8$^e$ | 7.2$^{ef}$ |
| 30 M (542 to 864 µm) | 15.0 | 20.2$^e$ | 50.0$^b$ | 4.5$^d$ | 7.5$^d$ |
| 40 M (381 to 542 µm) | 10.2 | 13.3$^f$ | 55.3$^a$ | 5.8$^b$ | 8.4$^b$ |
| Pan (<381 µm) | 18.8 | 11.0$^f$ | 55.9$^a$ | 6.4$^a$ | 9.2$^a$ |

NDF - Neutral Detergent Fiber, L - lighter fraction, H - heavier fraction. Composition values within each column and having same superscripted letter are not different. Values at 0.0% yield indicate composition of size fraction. The COVs were less than 15% for NDF, Protein, Fat and Ash.
* indicates those fractions whose COVs were greater than 15%.

Protein content increased in all of the size fractions where NDF increased. The amount of material (Wt %) in seven size fractions 10M, 12M, 16M, 20M, 30M, 40M and pan were 21.8, 9.4, 14.1, 10.8, 15.0, 10.2 and 18.8% respectively. The pan and 10M size fractions were not subjected to air classification.

Air classification of SBM size fractions was effective in separating fiber as indicated by higher NDF in lighter fractions compared to the corresponding heavier fractions and the unprocessed CSM (Table 14).

combination of sieving and air classification with low yield resulted in 1.3% of fiber being separated from CSM and NDF increased from 19.9% in unprocessed CSM to 53.5% in the fiber product (Table 15). Fiber separated for low yields of

TABLE 14

Composition and Wt % of fractions obtained by air classification of CSM size fraction (% db)

| Size | Fiber Yield (wt %) | NDF L | NDF H | Separation Factor | Protein L | Protein H | Fat L | Fat H | Ash L | Ash H | Separation Factor |
|---|---|---|---|---|---|---|---|---|---|---|---|
| 12 M | 0.0 | — | $27.8^b$ | | — | $45.5^b$ | — | $3.6^a$ | — | | $6.9^b$ |
| (>1,532 µm) | 4.1 | $69.6^a$ | $25.7^b$ | 6.6 | $15.3^d$ | $46.7^{a,b}$ | $1.8^{*b}$ | $3.8^a$ | $3.6^d$ | | $7.5^a$ |
| | 9.2 | $66.7^a$ | $27.3^a$ | 5.3 | $17.9^c$ | $48.5^a$ | $2.1^b$ | $3.7^a$ | $4.2^{*c}$ | | $7.5^a$ |
| 16 M | 0.0 | — | $31.3^b$ | | — | $43.9^b$ | — | $3.7^a$ | — | | $7.2^b$ |
| (1,130 to | 3.8 | $64.4^a$ | $31.9^b$ | 3.9 | $19.5^c$ | $45.9^{a,b}$ | $2.8^b$ | $3.5^a$ | $4.4^c$ | | $7.7^{*a}$ |
| 1,532 µm) | 8.2 | $64.2^a$ | $26.2^c$ | 5.0 | $19.7^{*c}$ | $47.7^a$ | $2.2^c$ | $3.7^a$ | $4.0^d$ | | $7.5^{a,b}$ |
| 20 M | 0.0 | — | $30.2^b$ | | — | $46.1^b$ | — | $3.8^{a,b}$ | — | | $7.2^{b,c}$ |
| (864 to | 3.3 | $46.4^a$ | $28.3^{b,c}$ | 2.2 | $31.5^c$ | $46.6^{a,b}$ | $3.6^{a,b}$ | $3.9^a$ | $6.7^c$ | | $7.6^{*a,b}$ |
| 1,130 µm) | 13.3 | $44.0^a$ | $25.6^c$ | 2.3 | $34.1^c$ | $49.8^a$ | $3.6^b$ | $3.9^a$ | $5.9^{*d}$ | | $7.9^a$ |
| 30 M | 0.0 | — | $20.2^b$ | | — | $50.0^{a,b}$ | — | $4.5^b$ | — | | $7.5^c$ |
| (542 to | 4.8 | $20.9^{a,b}$ | $20.6^{a,b}$ | 1.0 | $48.1^c$ | $50.6^a$ | $5.3^a$ | $4.6^a$ | $8.1^a$ | | $8.1^c$ |
| 864 µm) | 15.1 | $21.0^{a,b}$ | $21.9^a$ | 1.0 | $48.6^{b,c}$ | $50.4^a$ | $4.9^a$ | $4.6^a$ | $8.2^b$ | | $7.9^c$ |
| 40 M | 0.0 | — | $13.3^a$ | | — | $55.3^a$ | — | $5.8^a$ | — | | $8.4^c$ |
| (381 to | 6.5 | $14.7^a$ | $14.2^a$ | 1.0 | $51.2^c$ | $53.5^a$ | $5.7^a$ | $5.3^{a,b}$ | $9.0^{a,b}$ | | $8.7^{b,c}$ |
| 542 µm) | 16.2 | $13.8^a$ | $13.0^a$ | 1.1 | $55.3^b$ | $54.6^{a,b}$ | $5.7^{a,b}$ | $5.5^b$ | $9.2^a$ | | $8.8^b$ |

NDF - Neutral Detergent Fiber, L - lighter fraction, H - heavier fraction. Composition values within each size fraction and having same superscripted letter are not different. Values at 0.0% yield indicate composition of size fraction. COVs of Wt % NDF, Protein, Fat and Ash were less than 8, 10, 15 and 5%, respectively.
*indicates those fractions whose COVs were greater than the threshold values.

For 12M size fraction, the NDF increased from 27.8% in unprocessed CSM to 69.6% in the lighter fraction at lower yield (4.1%) and 66.7% at higher yield (9.2%) of lighter fraction (Table 14). At low yields of lighter fraction, NDF separation factor was 6.6 for 12M size fraction and gradually decreased through the size fractions from 3.9 (16M) to 1.0 (30M and 40M). NDF separation factors were low (1.0 to 1.1) for 30M and 40M size fractions, indicating that fiber separation was less effective for these two size fractions (Table 14). The moisture content of heavier fractions varied from 10.8 to 12.5%, and that of lighter fraction varied from 10.9 to 12.8%.

Air classification of 30M and 40M size fractions was not incorporated in calculation of compositions of products in Tables 15 and 16 because air classification did not result in effective fiber separation from 30M and 40M size fractions. The overall fiber separation from CSM and the composition of the final products, i.e. fiber and enhanced CSM, at low yield of lighter fraction, are reported in Table 15.

TABLE 15

Composition of products from processing of CSM with low lighter fraction yields (5%) in air classification (% wb). For calculations of products from CSM, unlike SBM, it was assumed that the 30M and 40M size fractions will not be air classified because separation factors for these two fractions were low.

| Product | Wt | NDF | Protein | Fat | Ash |
|---|---|---|---|---|---|
| Unprocessed CSM | 100.0 | 19.9 | 43.9 | 4.3 | 7.0 |
| Fiber | 1.3 | 53.5 | 19.0 | 2.4 | 4.2 |
| En CSM | 98.7 | 20.2 | 44.5 | 4.1 | 7.3 |

NDF - neutral detergent fiber,
En - Enhanced

The compositions of fiber and enhanced CSM in Table 15 and Table 16 were calculated from Table 13 and Table 14. The lighter fraction was only 1.3%. The NDF of fiber was high compared to unprocessed CSM, but the value did not vary much for enhanced CSM. Protein content decreased from 43.9 in unprocessed CSM to 19.0% in fiber and protein content increased by 0.6% in enhanced CSM.

Fiber products' quantity was higher, 3.5% by weight of unprocessed CSM, at high yields of lighter fraction (Table 16).

TABLE 16

Composition of products from processing of CSM with high lighter fraction yields (15%) in air classification (% wb). For calculations of products from CSM, unlike SBM, it was assumed that the 30M and 40M size fractions will not be air classified because separation factors for these two fractions were low.

| Product | Wt | NDF | Protein | Fat | Ash |
|---|---|---|---|---|---|
| Unprocessed CSM | 100.0 | 19.9 | 43.9 | 4.3 | 7.0 |
| Fiber | 3.5 | 49.4 | 22.1 | 2.4 | 4.2 |
| En CSM | 96.5 | 19.0 | 44.5 | 4.0 | 7.2 |

NDF - Neutral Detergent Fiber,
En - Enhanced.

The NDF increased from 19.9% of unprocessed CSM to 49.4% in fiber, the protein content decreased to 22.1% in fiber from 43.9% in unprocessed CSM, and protein content increased by 0.6% in enhanced CSM.

Wheat Middlings

Table 17 shows the WM composition and Wt % of size fractions obtained after sieving. The amount of material (Wt %) in seven size fractions 12M, 16M, 20M, 24M, 30M, 35M and pan were 11.4, 10.9, 14.6, 15.4, 8.8, 11.6 and 27.3%, respectively (Table 17).

TABLE 17

Composition and Wt % of fractions obtained by sieving Wheat Middlings (WM) (% db)

| Size | Wt | NDF | Protein | Fat | Ash |
|---|---|---|---|---|---|
| Unprocessed | 100.0 | 39.6[a] | 19.2[c] | 3.1[a] | 3.1[b] |
| 12 M (>1,532 μm) | 11.4 | 42.9[a] | 19.0[b] | 3.3[a] | 5.7[a] |
| 16 M (1,130 to 1,532 μm) | 10.9 | 42.6[a] | 19.7[b,c] | 3.2[a] | 5.6[a] |
| 20 M (864 to 1,130 μm) | 14.6 | 39.3[a] | 20.5[a,b] | 3.5[a] | 5.3[a,b] |
| 24 M (704 to 864 μm) | 15.4 | 39.8[a] | 20.0[a,b,c] | 3.3*[a] | 5.4[a] |
| 30 M (542 to 704 μm) | 8.8 | 42.8[a] | 19.1[c] | 3.8[a] | 5.3[a,b] |
| 35 M (447 to 542 μm) | 11.6 | 40.0[a] | 19.8[b,c] | 3.7[a] | 4.7[b] |
| Pan (<447 μm) | 27.3 | 29.7[b] | 20.9[a] | 3.3[a] | 4.0[c] |

NDF - Neutral Detergent Fiber, L - lighter fraction, H - heavier fraction. Composition values within each column and having same superscripted letter are not different. Values at 0.0% yield indicate composition of size fraction. The COVs were less than 15% for NDF, Protein, Fat and Ash.
*indicates those fractions whose COVs were greater than 15%.

Sieving of WM resulted in the change of NDF and protein content of size fractions, but there was no particular trend.

Air classification of WM resulted in an increase of NDF in lighter fractions at high and low yields of lighter fractions compared to their corresponding heavier fractions and the unprocessed WM (Table 18).

TABLE 18

Composition and Wt % of fractions obtained by air classification of wheat middlings (WM) (% db)

| Size | Fiber Yield (Wt %) | NDF L | NDF H | NDF Separation Factor | Protein L | Protein H | Fat L | Fat H | Ash Separation Factor | Ash L |
|---|---|---|---|---|---|---|---|---|---|---|
| 12 M (>1,532 μm) | 0.0 | — | 42.9[c] | — | — | 19.0[a] | — | 3.3[a] | — | 5.7[c] |
| | 5.8 | 56.3[a] | 49.0[b] | 1.3 | 15.3[c] | 18.2[b] | 2.6[a] | 3.2[a] | 7.1[a,b] | 6.6[b] |
| | 13.4 | 54.7[a] | 49.2[b] | 1.2 | 17.7[b] | 18.0[b] | 3.3*[a] | 2.9[a] | 7.3[a] | 6.7[b] |
| 16 M (1,130 to 1,532 μm) | 0.0 | — | 42.6[c] | — | — | 19.7[a] | — | 3.2[a] | — | 5.6[c] |
| | 6.6 | 55.4[a] | 47.9[b] | 1.4 | 14.3[d] | 19.4[a,b] | 2.6[b] | 3.3[a] | 6.2[b,c] | 6.1[b,c] |
| | 11.9 | 54.4[a] | 46.6[b] | 1.4 | 17.1[c] | 18.9[b] | 2.3[b] | 3.2[b] | 6.8[a] | 6.4[a,b] |
| 20 M (864 to 1,130 μm) | 0.0 | — | 39.3[c] | — | — | 20.5[a] | — | 3.5[a] | — | 5.3[c,d] |
| | 7.2 | 57.5[a] | 47.2[b] | 1.5 | 12.6[c] | 19.2[a] | 2.3[b,c] | 2.8[a,b] | 5.0[d] | 6.0[b] |
| | 13.0 | 55.5[a] | 43.7[b] | 1.6 | 15.4[a] | 19.2[a] | 2.0*[c] | 3.0[a] | 5.7[b,c] | 6.7[a] |
| 24 M (704 to 864 μm) | 0.0 | — | 39.8[d] | — | — | 20.0[a] | — | 3.3[a] | — | 5.4[a,b] |
| | 4.9 | 63.0[a] | 44.6[c,d] | 2.1 | 10.4[c] | 20.3[a] | 1.3*[b] | 2.9[a] | 3.9*[c] | 5.8[a,b] |
| | 18.0 | 52.7[b] | 47.9[c,b] | 1.2 | 15.6[b] | 19.0[a] | 2.7[a] | 3.0*[a] | 5.2[b] | 6.1*[a] |
| 30 M (542 to 704 μm) | 0.0 | — | 42.8[c] | — | — | 19.1[b] | — | 3.8[a] | — | 5.3[b,c] |
| | 7.1 | 59.6[a] | 41.4[d] | 2.1 | 11.5[d] | 20.8[a] | 1.7[c] | 3.6*[a] | 4.1[d] | 5.6[b] |
| | 16.8 | 54.3[b] | 48.1[c] | 1.3 | 14.9[c] | 18.4[b] | 2.6[b] | 2.9*[b] | 5.0[c] | 6.2[a] |
| 35 M (447 to 542 μm) | 0.0 | — | 40.0[d] | — | — | 19.8[b] | — | 3.7[a] | — | 4.7[c] |
| | 8.7 | 57.5[a] | 38.9[d] | 2.1 | 12.1[e] | 21.0[a] | 1.9[d] | 3.2[a,b] | 4.3[d] | 5.1[b] |
| | 17.1 | 52.6[b] | 46.0[c] | 1.3 | 14.6[d] | 18.6[c] | 2.5[c,d] | 2.9[b,c] | 4.8[c] | 6.2[a] |

NDF - Neutral Detergent Fiber, L - lighter fraction, H - heavier fraction. Composition values within each size fraction and having same superscripted letter are not different. Values at 0.0% yield indicate composition of size fraction. COVs of Wt % NDF, Protein, Fat and Ash were less than 8, 10, 15 and 5% respectively.
*indicates those fractions whose COVs were greater than the threshold values.

The overall fiber separation from WM and the composition of the final products, i.e. fiber and enhanced WM, at low and high yields of lighter fraction, are reported in Table 19 and Table 20. The compositions of fiber and enhanced SBM in Table 19 and Table 20 were calculated from Table 17 and Table 18. The combination of sieving and air classification with low yield resulted in 4.8%, by weight of fiber being separated from WM and NDF increased from 34.7% in unprocessed WM to 52.0% in the fiber product (Table 19).

TABLE 19

Composition of products from processing of WM with low lighter fraction yields (5%) in air classification (% wb)

| Product | Wt | NDF | Protein | Fat | Ash |
|---|---|---|---|---|---|
| Unprocessed WM | 100.0 | 34.7 | 16.9 | 2.7 | 4.2 |
| Fiber | 4.8 | 52.0 | 11.3 | 1.8 | 4.5 |
| En WM | 95.2 | 35.8 | 17.7 | 2.8 | 4.7 |

NDF - Neutral Detergent Fiber, En - Enhanced.

At higher yield of lighter fraction, fiber product was higher (11.0% by weight) compared to the low yield of lighter fraction but at the cost of fiber purity (NDF content); lower NDF (47.9%) in fiber indicates that more non-fiber was carried over along with fiber (Table 20).

TABLE 20

Composition of products from processing of WM with high lighter fraction yields (15%) in air classification (% wb)

| Product | Wt | NDF | Protein | Fat | Ash |
|---|---|---|---|---|---|
| Unprocessed WM | 100.0 | 34.7 | 16.9 | 2.7 | 4.2 |
| Fiber | 11.0 | 47.9 | 14.0 | 2.3 | 5.0 |
| En WM | 89.0 | 36.6 | 17.1 | 2.7 | 5.0 |

NDF - Neutral Detergent Fiber, En - Enhanced.

Discussion

Trends in compositions with respect to lighter fraction yield, observed in Tables 10, 14 and 18, were similar to those observed for DDGS (Srinivasan et al., 2005). NDF separation factors were lower at higher lighter fraction yields than at lower lighter fraction yields, indicating better fiber separation at lower air velocities due to lesser carry over of non-fiber components. At lower lighter fraction yields, protein contents in heavier fractions were equal to or higher than that of size fractions. At higher lighter fraction yields, protein contents of heavier fractions were higher than that of size fraction due to higher carry-over of fiber material by air. Lighter fractions had a lower fat content at low yields compared to the size fractions and same fat content as size fractions at higher yields of lighter fractions. The fat content of heavier fractions remained the same as that of size fractions, and no trend was observed at low and high yields of lighter fraction.

Thus, lighter fractions had lower protein, lower fat and higher NDF than their corresponding size fractions. The heavier fractions had higher protein, higher fat and lower NDF than their corresponding size fractions. Increase in lighter fraction yields increased protein content in heavier fraction, but NDF separation factor decreased, and NDF of lighter fraction decreased. These trends are similar to those observed for DDGS by Srinivasan et al. (2005). NDF separation factors were lower for WM compared to CSM and SBM, indicating that Elusieve processing was not as effective in fiber separation for WM (Tables 10, 14 and 18). Elusieve processing increased protein content highest for enhanced DDGS (1.8 to 2.4%), followed by enhanced SBM (1.4 to 2.0%), CSM (0.6%) and WM (0.2 to 0.7%) (Tables 11, 12, 15, 16, 19 and 20) (Srinivasan et al., 2006). Thus, fiber separation was more useful and effective for DDGS and SBM compared to CSM and WM in terms of increasing protein content in the enhanced feeds.

Conclusions

In this study, the combination of sieving and air-classification was evaluated for fiber separation from SBM, CSM and WM. The experiments were conducted to separate fiber at different yields of lighter fractions. At low yields of lighter fraction (5% yields), the quantities of the fiber separated were 3.7, 1.3 and 4.8% by weight of SBM, CSM and WM, respectively. At high yields of lighter fractions (15% yields), the quantities of fiber separated were 8.9, 3.5 and 11% by weight of SBM, CSM and WM, respectively.

Similar to trends observed for DDGS, fiber purity (NDF content) was higher at lower yields of lighter fractions as compared with that at high yields of lighter fraction. Lighter fractions had lower protein, lower fat and higher NDF than their corresponding size fractions. The heavier fractions had higher protein, higher fat and lower NDF than their corresponding size fractions. Elusieve processing increased protein content highest for enhanced DDGS (1.8 to 2.4%), followed by enhanced SBM (1.4 to 2.0%), CSM (0.6%) and WM (0.2 to 0.7%). Thus, fiber separation was more useful and effective for DDGS and SBM, compared to CSM and WM, in terms of increasing protein content in the enhanced feeds. Separation factors of WM size fractions were very low, and there was a substantial amount of fiber remaining in the heavier fractions even after sieving and air classification.

Future studies on nutritional characteristics of enhanced SBM and enhanced CSM for poultry, swine, and pets need to be pursued. Research on utilization of fiber products from SBM, CSM and WM in ruminant diets also needs to be carried out.

EXAMPLE 11

The process described herein, the combination of sieving and air classification (elutriation), was developed at laboratory scale to separate fiber from DDGS and produce two valuable products: 1) Enhanced DDGS with lower fiber and higher protein and fat contents that could be more suitable for feeding chicken and pigs, and 2). Fiber (Srinivasan et al., 2005; Srinivasan et al., 2008). In this process, which we call the Elusieve process, DDGS is sieved into four or five different sieve fractions and fiber is separated from the three or four largest sieve fractions by air classification (Srinivasan et al., 2005; Srinivasan et al., 2008). The smallest sieve fraction from DDGS, which comprises 30 to 40 weight % of the original DDGS, is not subjected to air classification because the sieve fraction contains lower fiber (NDF; neutral detergent fiber), higher protein and higher fat contents. Fiber particles were carried selectively in each sieve fraction, at low air velocities, as they had low terminal velocities due to their flat shape and low mass (Srinivasan and Singh, 2008).

The Elusieve process was effective in separating fiber from commercial DDGS samples in laboratory scale. Economics analysis for implementation of the Elusieve process in an existing dry grind plant processing corn at the rate of 2,030 metric tonnes/day (80,000 bushels/day) estimated that the total capital investment required would be $1.4 million, based on equipment purchase cost of $0.43 million (Srinivasan et al., 2006). Nutritional studies on poultry have shown increased weight gain for birds fed with DDGS from the Elusieve process (Kim et al., 2007; Loar et al., 2008; Martinez-Amezuca et al., 2007). Low capital investment is needed for the Elusieve process because of its simplicity, non-intrusiveness and use of conventional equipment. A significant portion of US fuel ethanol production comes from farmer owned cooperatives and low capital investment is an important basis for the preference of dry grind process over the wet milling process by these cooperatives (Belyea et al., 2004; RFA, 2008). Elusieve process' value addition to coproducts from fuel ethanol production and its low capital investment requirements have made it a technology of interest for plant scale implementation.

In the laboratory scale apparatus, processing was carried out in batch operation and air classification was carried out in an elutriation column (internal diameter of 63 mm or 155 mm) that was custom built. In industrial scale implementation of the Elusieve process, commercial sifters and aspirators would be used. There is a need to evaluate the Elusieve process in pilot scale in order to determine its effectiveness using commercial equipment and to verify its operability in continuous mode. In this study, a pilot plant was assembled to evaluate fiber separation from DDGS on a continuous basis using commercial sifter and aspirators. The sifter and aspirators were not custom made and were procured off-the-shelf from equipment manufacturers. In an embodiment evaluating fiber separation from commercial DDGS material in the pilot plant, we compare the results with those obtained for laboratory scale and obtain operating experience.

Materials and Methods

Pilot Plant and Nomenclature for Fractions and Products

Figure 16:
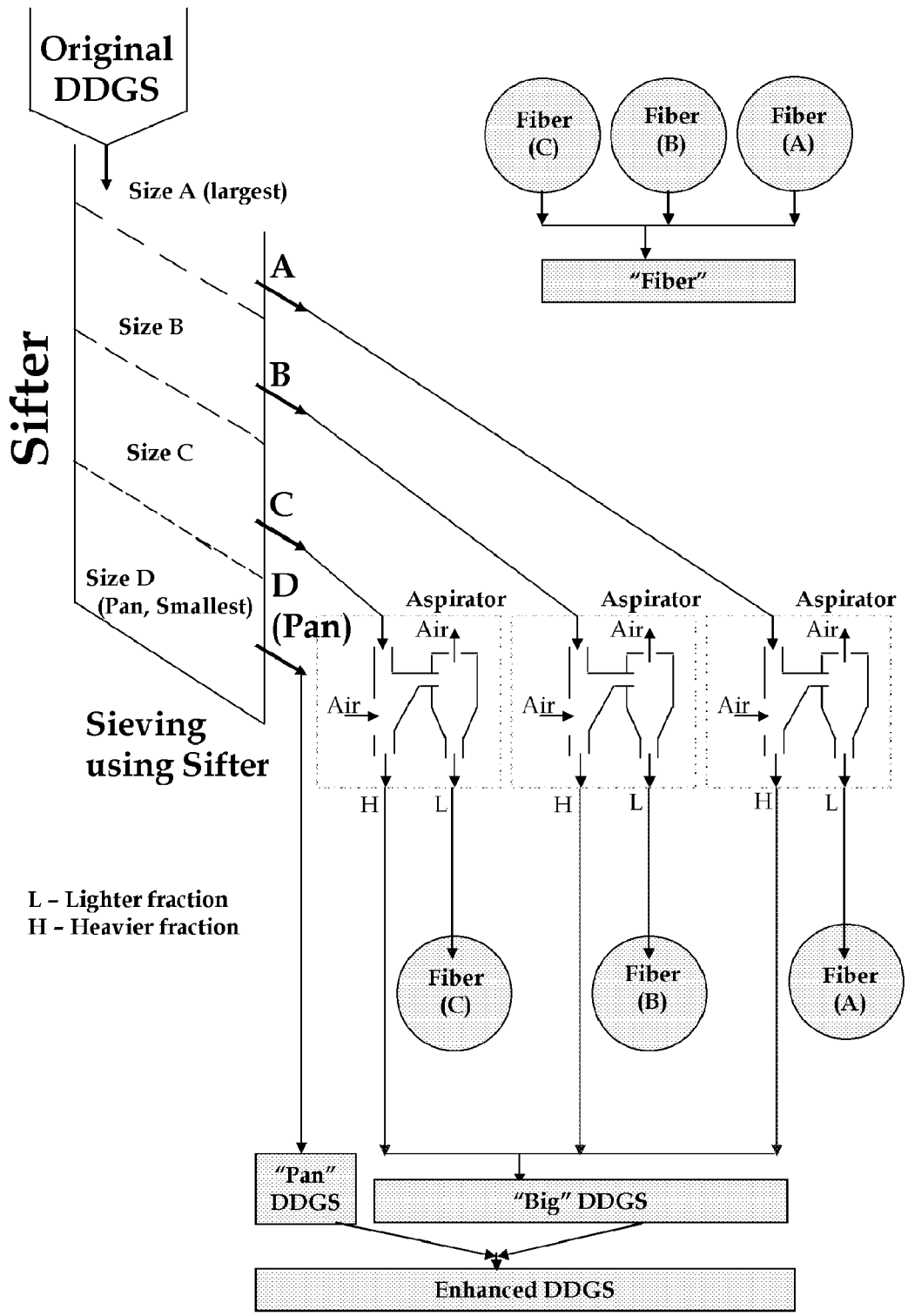
FIG. 16: shows a schematic of the Elusieve process for fiber separation from DDGS.

A rectangular rotary sifter (Model 484, Gump, Savannah, Ga.) with a sieving area of 1.8 m2 (19 ft2) per deck and consisting of three decks for stack sieving was used to produce four sieve fractions, which are denoted as A (largest size), B, C and D (smallest size) (FIG. 16). The opening size for screens was chosen such that each of the A, B and C sieve fractions would be 20% by weight of the original DDGS (Srinivasan et al., 2005). The D sieve fraction (smallest size) is also denoted as a product called "Pan" DDGS.

Figure 17:
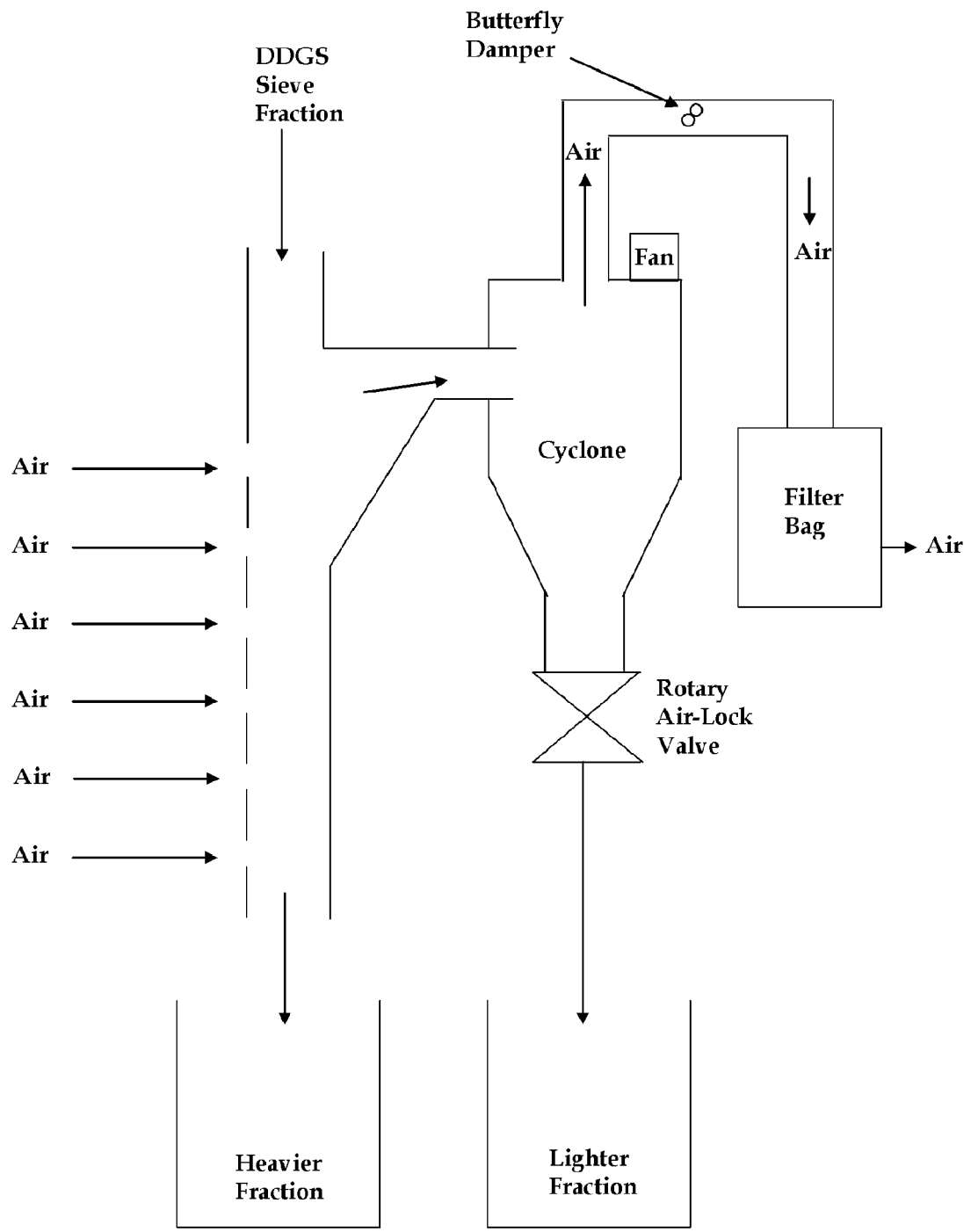
FIG. 17: shows a schematic of a multi-aspirator for air classification of DDGS sieve fractions

The A, B and C sieve fractions were air classified using three multi-aspirators (Model VJ8X6, Kice, Wichita, Kans.). The multi-aspirator comprises a material feeding section, through which the DDGS sieve fraction is fed, and an air-inlet section through which air is sucked into the aspirator by a fan (FIG. 17). The fan for the multi-aspirator that was used to aspirate the large sieve fraction was operated by a 1.1 kW (1.5 hp) motor and the fans in the other two aspirators were operated by 0.6 kW (0.75 hp) motors. A higher rating fan was used for the large sieve fraction because of the higher air velocities needed to separate fiber from large sieve fraction compared to the other fractions. The air carries the lighter particles in the sieve fraction to the cyclone section. The remaining part of the sieve fractions, which are the heavier particles and are not carried by the air, flows straight through the feeding section into a collection drum. The lighter fraction collects at the bottom of the cyclone section and the rotary air-lock valve in the cyclone outlet enables continuous operation by letting the lighter fraction flow into a collection drum. The air from the cyclone flows out through a filter bag, which is used to retain any residual particles. A butterfly type damper is available in the air flow duct to adjust the air flow in the aspirator and thus, control the yield of lighter fraction from the sieve fraction (FIG. 17).

The product obtained by mixing fiber fractions from the three largest sieve fractions, namely the A, B and C fiber fractions, is called the "Fiber" product. The product obtained by mixing the heavier fractions from the three largest sieve fractions, namely the A, B and C heavier fractions, is called "Big" DDGS product because it is the bigger sized portion of the DDGS compared to the other product, Pan DDGS. The product obtained by mixing the Big DDGS and Pan DDGS is called Enhanced DDGS, which is the same as the material referred as Enhanced DDGS in earlier works on the Elusieve process (Srinivasan et al., 2005; Srinivasan et al., 2006; Srinivasan et al., 2008). In this work, we suggest production of three products from the Elusieve process, Pan DDGS, Big DDGS and Fiber, instead of just two products, Enhanced DDGS and Fiber.

DDGS Processing and Experimental Scheme

Commercial DDGS material was obtained from a local feed mill (Prairie Mills, Prairie, Miss.). The pilot plant was tested on three different DDGS materials, DDGS-1, DDGS-2 and DDGS-3. The presence of a few wheat kernels along with corn kernels in the DDGS materials suggests that the dry grind plant supplying the DDGS could be processing a mixture of corn and wheat. The moisture contents of DDGS-1, DDGS-2 and DDGS-3 were 12.9, 11.5 and 12.8%, respectively. The effect of moisture content on fiber separation from DDGS was not studied in this work. DDGS was gravity fed from a hopper to the sifter, through a manual gate valve, at a rate of 0.25 kg/s (1 ton/hr).

The quantity of DDGS fed in each processing batch varied depending on the availability of laboratory infrastructure and DDGS material. Within each processing batch, the yields of fractions were fixed. For batch 1 processing of DDGS-1, 312 kg was processed in 25 min at low lighter fraction yields of 6 to 7% (Table 21).

TABLE 21

(a)

| DDGS | Material Description | Size (μm) | Wt (kg) H | Wt (kg) L | Wt % of sieve fraction Wt % | Yield (L) (%) Yield | NDF H | NDF L | Sep. Factor |
|---|---|---|---|---|---|---|---|---|---|
| DDGS-1 | 1-1A | >1,184 | 48.1 | 3.7 | 15.9 | 7.1 | 28.7a | 55.1b | 3.0 |
| (Batch 1, | 1-1B | 868 to 1,184 | 64.9 | 5.1 | 21.5 | 7.3 | 32.0a | 52.9b | 2.4 |
| Low Lighter | 1-1C | 582 to 868 | 74.4 | 4.4 | 24.2 | 5.6 | 30.3a | 52.0b | 2.5 |
| Fraction | 1-1D | <582 | 124.9 | | 38.4 | NA | 26.3 | | NA |
| Yields) | DDGS-1 | All | 312.3 | | 100.0 | NA | 29.8 | | NA |
| DDGS-1 | 1-2A | >1,184 | 10.8 | 2.1 | 20.4 | 15.9 | 28.8a | 50.6b | 2.5 |
| (Batch 2, | 1-2B | 868 to 1,184 | 9.9 | 4.0 | 22.1 | 28.9 | 29.6a | 46.0b | 2.0 |
| High | 1-2C | 582 to 868 | 12.5 | 3.6 | 25.5 | 22.3 | 27.8a | 42.5b | 1.9 |
| Lighter | 1-2D | <582 | 20.2 | | 32.0 | NA | 24.0 | | NA |
| Fraction Yields) | DDGS-1 | All | 53.5 | | 100.0 | NA | 29.8 | | NA |
| DDGS-2 | 2-1A | >1,184 | 42.8 | 7.7 | 12.3 | 15.2 | 24.1a | 42.3b | 2.3 |
| (Batch 1) | 2-1B | 868 to 1,184 | 59.5 | 7.3 | 16.2 | 10.9 | 24.7a | 48.7b | 2.9 |
| | 2-1C | 582 to 868 | 83.1 | 14.3 | 23.7 | 14.7 | 27.6a | 44.4b | 2.1 |
| | 2-1D | <582 | 196.8 | | 47.8 | NA | 26.6 | | NA |
| | DDGS-2 | All | 382.2 | | 100.0 | NA | 27.6 | | NA |
| DDGS-3 | 3-1A | >1,041 | 89.1 | 12.7 | 14.9 | 12.5 | 27.9a | 48.8b | 2.5 |
| (Batch 1, | 3-1B | 680 to 1,041 | 163.0 | 19.5 | 26.7 | 10.7 | 29.3a | 49.2b | 2.3 |
| Low Lighter | 3-1C | 470 to 680 | 139.3 | 25.1 | 24.1 | 15.3 | 28.9a | 38.6b | 1.5 |
| Fraction | 3-1D | <470 | 234.5 | | 34.3 | NA | 25.5 | | NA |
| Yields) | DDGS-3 | All | 625.9 | | 100.0 | NA | 29.0 | | NA |
| DDGS-3 | 3-2A | >1,041 | 166.4 | 30.2 | 15.7 | 15.4 | 26.7a | 50.6b | 2.8 |
| (Batch 2, | 3-2B | 680 to 1,041 | 308.6 | 52.0 | 28.8 | 14.4 | 27.0a | 48.5b | 2.5 |
| High | 3-2C | 470 to 680 | 211.1 | 72.2 | 22.7 | 25.5 | 26.0a | 37.1b | 1.7 |
| Lighter | 3-2D | <470 | 409.7 | | 32.8 | NA | 26.5 | | NA |
| Fraction Yields) | DDGS-3 | All | 1095.8 | | 100.0 | NA | 28.7 | | NA |

(b)

| DDGS | Protein H | Protein L | Fat H | Fat L | Ash H | Ash L | Moisture (% wb) H | Moisture (% wb) L |
|---|---|---|---|---|---|---|---|---|
| DDGS-1 | 28.0a | 15.6b | 12.4a | 5.3b | 4.4a | 3.9b | 11.2a | 11.0a |
| (Batch 1, | 28.1a | 16.2b | 11.4a | 5.5b | 4.6a | 4.0b | 11.2a | 11.2a |
| Low Lighter | 29.4a | 17.1b | 10.6a | 6.0b | 4.6a | 4.0b | 11.4a | 11.4a |

TABLE 21-continued

| Sample | | | | | | | | |
|---|---|---|---|---|---|---|---|---|
| Fraction | 33.8 | | 9.2 | | 4.9 | | 12.1 | |
| Yields) | 30.1 | | 10.3 | | 4.7 | | 11.6 | |
| DDGS-1 | 29.8a | 19.2b | 12.7a | 6.2b | 4.5a | 3.8b | 12.1a | 11.9a |
| (Batch 2, | 30.5a | 21.8b | 11.5a | 7.4b | 4.4a | 4.0b | 12.2a | 12.1a |
| High | 32.2a | 22.9b | 10.5a | 7.9b | 4.6a | 4.2b | 12.3a | 12.1a |
| Lighter | 36.5 | | 9.9 | | 4.8 | | 13.4 | |
| Fraction | 31.3 | | 10.4 | | 4.5 | | 12.6 | |
| Yields) | | | | | | | | |
| DDGS-2 | 27.0a | 23.0b | 10.6a | 5.7b | 5.3a | 4.1b | 12.2a | 12.9b |
| (Batch 1) | 28.9a | 17.5b | 11.0a | 5.2b | 4.8a | 4.1b | 12.4a | 13.4b |
|  | 31.3a | 21.3b | 8.6a | 5.5b | 4.8a | 4.4b | 12.9a | 13.1a |
|  | 35.2 | | 6.8 | | 4.6 | | 12.9 | |
|  | 31.6 | | 8.1 | | 4.7 | | 12.8 | |
| DDGS-3 | 30.3a | 20.6b | 10.7a | 5.1b | 4.3a | 3.6b | 12.2a | 12.4a |
| (Batch 1, | 32.0a | 20.0b | 9.4a | 5.5b | 4.2a | 3.8b | 12.3a | 12.5a |
| Low Lighter | 34.8a | 28.5b | 7.8a | 6.1b | 4.3a | 4.0b | 12.4a | 12.5a |
| Fraction | 39.0 | | 6.6 | | 4.7 | | 12.7 | |
| Yields) | 34.1 | | 7.9 | | 4.4 | | 12.4 | |
| DDGS-3 | 30.5a | 16.6b | 10.7a | 4.8b | 4.4a | 3.6b | 11.9a | 12.3b |
| (Batch 2, | 32.3a | 19.9b | 9.8a | 4.9b | 4.5a | 3.9b | 11.9a | 12.6b |
| High | 37.0a | 27.9b | 8.1a | 6.5b | 4.6a | 3.9b | 12.3a | 12.4a |
| Lighter | 39.6 | | 7.0 | | 4.8 | | 12.6 | |
| Fraction | 34.1 | | 8.2 | | 4.5 | | 12.3 | |
| Yields) | | | | | | | | |

NDF - neutral detergent fiber,
H - heavier fraction,
L - lighter fraction,
NA - not applicable,
Sep. Factor - separation factor.
Values are reported as means of three samples from each fraction during processing. Values for the same DDGS, same sieve fraction and same composition with the same superscript are not different (p < 0.05).
Values for original DDGS are calculated from composition of individual fractions.
Coefficients of variation (CV) were less than 11%.

For batch 2 processing of DDGS-1, 53 kg was processed in 5 min at higher lighter fraction yields of 16 to 29%. DDGS-2 was processed in only one batch; 382 kg was processed in 30 min at lighter fraction yields of 11 to 15%. For batch 1 processing of DDGS-3, 626 kg was processed in 45 min at lighter fraction yields of 11 to 15%. For batch 2 processing of DDGS-3, 1096 kg was processed in 75 min at higher lighter fraction yields of 15 to 25% (Table 21). When referring to the fractions from the processing batches, the terminology used is in the following sequence; DDGS material, batch number, sieve fraction and L or H to refer to the lighter or heavier fractions. For example, 1-1AH refers to DDGS-1, batch 1, A sieve fraction and heavier fraction from the A sieve fraction.

Compositions of fractions were obtained by collecting three samples from each of the collection drums. The samples were ground to a fine powder using a coffee grinder prior to analysis to avoid particle segregation, which has been observed for DDGS by Ileleji et al. (2007). Analyses of samples were carried out at a commercial laboratory (Midwest Labs, Omaha, Nebr.). Neutral detergent fiber (NDF) content was determined using the procedure of Van Soest et al. (1991). Samples were analyzed for total nitrogen (AOAC 2003, Method 990.03). Crude protein content was calculated as total N×6.25. Samples were also analyzed for crude fat (AOAC 2003, Method 920.39) and ash (AOAC 2003, Method 942.05). Moisture content was determined using the two-stage convection oven method (AACC International 2000, Method 44-18). The composition of products from Elusieve processing and original DDGS were calculated using the compositions of individual fractions that comprise the products.

NDF Separation Factor

NDF separation factor for elutriation is defined as the ratio of the NDF %/Non-NDF % of the lighter fraction to the NDF %/Non-NDF % of the heavier fraction (Srinivasan et al., 2005). It is calculated as:

$$[\text{NDF \%}/(100-\text{NDF \%})]\text{Lighter fraction}/[\text{NDF \%}/(100-\text{NDF \%})]\text{Heavier fraction}.$$

NDF separation factor indicates the selectivity of air in carrying fiber rather than nonfiber. A high NDF separation factor indicates that the selectivity of air in carrying fiber is high.

Statistical Analyses

Analysis of variance (ANOVA) and Tukey's test (SAS Institute, Cary, N.C.) were used to compare means of compositions of three samples from Elusieve fractions in each processing batch. Within each processing batch, the yields were fixed. There were no replicates for yield of fractions in each processing batch. Statistical significance level was 5% ($p<0.05$). Coefficients of variation for all compositions were less than 11%.

Results and Discussion

Elusieve Fractions

Lighter fractions from air classification of sieve fractions had higher fiber (NDF) content than corresponding heavier fractions. Heavier fractions had higher protein, fat and ash contents than corresponding lighter fractions (Table 21). NDF separation factors were more than 1.0 indicating fiber separation from sieve fractions. Similar trends were observed in laboratory scale studies also (Srinivasan et al., 2005; Srinivasan et al., 2008). The smallest sieve fraction, D, comprising 32 to 48% by weight of DDGS, contained lower fiber (NDF) and higher protein contents than the corresponding original DDGS (Table 21). Moisture contents of fractions varied from 11.0 to 13.4%. Coefficients of variation (CV) were less than 11% for sample compositions.

At higher lighter fraction yields from the same sieve fractions, the heavier fractions had higher protein, higher fat, and lower NDF contents than for heavier fractions at lower lighter fraction yields, indicating carry over of higher quantities of fiber from the sieve fractions at higher air velocities (Table 21). Similar trends were observed in laboratory scale studies also (Srinivasan et al., 2005; Srinivasan et al., 2008). For example; for 3-2CH at higher lighter fraction yield of 25.5%, had higher protein content of 37.0%, higher fat content of 8.1%, and lower NDF of 26.0% compared to 3-1CH at lower Elusieve Products Among the products from the same DDGS, Pan DDGS had the highest protein content and also had the lowest fiber (NDF) content (Table 22).

TABLE 22

Composition (% db) and weight % of products obtained by pilot scale Elusieve processing of DDGS. (Values are calculated from compositions of fractions reported in Table 21).

| DDGS | Material Description | Wt % of Original DDGS | Protein | Fat | NDF | Ash | Moisture (% wb) |
|---|---|---|---|---|---|---|---|
| DDGS-1 (Batch 1, Low Lighter Fraction Yields) | Original DDGS | 100.0 | 30.1 | 10.3 | 29.8 | 4.7 | 11.6 |
| | Enhanced DDGS | 95.9 | 30.7 | 10.5 | 28.8 | 4.7 | 11.6 |
| | Big DDGS | 57.6 | 28.6 | 11.4 | 30.5 | 4.5 | 11.3 |
| | Pan DDGS | 38.4 | 33.8 | 9.2 | 26.3 | 4.9 | 12.1 |
| | Fiber | 4.1 | 16.3 | 5.6 | 53.2 | 4.0 | 11.2 |
| DDGS-1 (Batch 2, High Lighter Fraction Yields) | Original DDGS | 100.0 | 31.3 | 10.4 | 29.8 | 4.5 | 12.6 |
| | Enhanced DDGS | 84.7 | 33.0 | 10.9 | 26.9 | 4.6 | 12.6 |
| | Big DDGS | 52.7 | 30.9 | 11.5 | 28.7 | 4.5 | 12.2 |
| | Pan DDGS | 32.0 | 36.5 | 9.9 | 24.0 | 4.8 | 13.4 |
| | Fiber | 15.3 | 21.6 | 7.3 | 45.7 | 4.0 | 12.1 |
| DDGS-2 (Batch 1) | Original DDGS | 100.0 | 31.6 | 8.1 | 27.6 | 4.7 | 12.8 |
| | Enhanced DDGS | 92.9 | 32.5 | 8.3 | 26.2 | 4.8 | 12.8 |
| | Big DDGS | 45.1 | 29.5 | 9.8 | 25.9 | 4.9 | 12.6 |
| | Pan DDGS | 47.8 | 35.2 | 6.8 | 26.6 | 4.6 | 12.9 |
| | Fiber | 7.1 | 20.8 | 5.5 | 44.9 | 4.2 | 13.1 |
| DDGS-3 (Batch 1, Low Lighter Fraction Yields) | Original DDGS | 100.0 | 34.1 | 7.9 | 29.0 | 4.4 | 12.4 |
| | Enhanced DDGS | 91.6 | 35.0 | 8.2 | 27.6 | 4.4 | 12.4 |
| | Big DDGS | 57.3 | 32.6 | 9.1 | 28.8 | 4.3 | 12.3 |
| | Pan DDGS | 34.3 | 39.0 | 6.6 | 25.5 | 4.7 | 12.7 |
| | Fiber | 8.4 | 23.9 | 5.4 | 44.5 | 3.8 | 12.5 |
| DDGS-3 (Batch 2, High Lighter Fraction Yields) | Original DDGS | 100.0 | 34.1 | 8.2 | 28.7 | 4.5 | 12.3 |
| | Enhanced DDGS | 87.6 | 35.7 | 8.6 | 26.6 | 4.6 | 12.2 |
| | Big DDGS | 54.9 | 33.3 | 9.5 | 26.6 | 4.5 | 12.0 |
| | Pan DDGS | 32.8 | 39.6 | 7.0 | 26.5 | 4.8 | 12.6 |
| | Fiber | 12.4 | 23.0 | 5.6 | 43.6 | 3.9 | 12.5 | lighter fraction yield of 15.3%, with protein content of 34.8%, fat content of 7.8% and NDF of 28.9%.

At lower lighter fraction yields from the same sieve fractions, NDF separation factors and NDF of lighter fractions were similar or higher than for higher lighter fraction yields, indicating higher selectivity of air to carry fiber at lower air velocities (Table 21). Similar trends were observed in laboratory scale studies also (Srinivasan et al., 2005; Srinivasan et al., 2008). For example; for 1-1AL at low lighter fraction yield of 7.1%, lighter fraction NDF was 55.1% and separation factor was 3.0, which were higher compared to 1-2AL at higher lighter fraction yield of 15.9%, with lighter fraction NDF of 50.6% and separation factor of 2.5.

At higher lighter fraction yields from the same sieve fractions, protein and fat contents of lighter fractions were similar or higher compared to protein and fat contents of lighter fractions at lower yields, indicating carry over of higher quantity of nonfiber at higher air velocities (Table 21). Similar trends were observed in laboratory scale studies also (Srinivasan et al., 2005; Srinivasan et al., 2008). For example; 1-2CL at higher lighter fraction yield of 22.3%, with protein content of 22.9% and fat content of 7.9%, which were higher compared to 1-1CL at lower lighter fraction yield of 5.6%, with protein content of 17.1% and fat content of 6.0%

The weight % of all DDGS-3 sieve fractions for both processing batches were similar, indicating repeatability of sifter performance (Table 21). The weight % of medium and small fractions for both batches of DDGS-1 were similar, but the weight % of large and pan fractions for the two batches of DDGS-1 were slightly different perhaps because of the low quantity (53.5 kg) of DDGS processed in batch 2 (Table 21).

Pan DDGS had slightly lower fat content than the corresponding original DDGS. The difference in protein contents of Pan DDGS and original DDGS was 3.6 to 5.5%. Difference between protein content of Pan DDGS and original DDGS was higher (4.9 to 5.5%) for the three cases where the weight % of Pan DDGS was lower (32.0, 32.8 and 34.3%) compared to the difference in protein contents (3.6 to 3.7%) for the two cases where the weight % of Pan DDGS was higher (38.4 and 47.8%) (Table 22). The opening of the smallest screen determines the weight % of Pan DDGS and hence, choosing a smaller opening screen for the smallest screen in the sifter would result in Pan DDGS with higher protein contents.

Enhanced DDGS had higher protein and fat contents than corresponding original DDGS and lesser protein and fat contents than corresponding Pan DDGS (Table 22). Difference between protein contents of Enhanced DDGS and original DDGS was higher when weight % of Fiber removed was higher. For example; difference between protein content of Enhanced DDGS and original DDGS was higher (1.6 and 1.7%) for the two cases where the weight % of Fiber was higher (12.4 and 15.3%) compared to the difference in protein contents (0.6 to 0.9%) for the three cases where the weight % of Fiber was lower (4.1 to 8.4%) (Table 22).

Big DDGS had slightly lower protein content (difference of −0.4 to −2.1%) compared to corresponding original DDGS, but Big DDGS also had higher fat content (difference of 1.1 to 1.7%) compared to corresponding original DDGS. Similar to results for Enhanced DDGS, difference between protein contents of Big DDGS and original DDGS was higher when weight % of Fiber removed was higher. For example; difference between protein content of Big DDGS and original DDGS was higher (−0.4 and −0.8%) for the two cases where the weight % of Fiber was higher (12.4 and 15.3%) compared to the difference in protein contents (−1.5 to −2.2%) for the three cases where the weight % of Fiber was lower (4.1 to 8.4%) (Table 22). Fat contents for Big DDGS were higher when higher weight % of Fiber was removed from the same DDGS. For example; for DDGS-3, Big DDGS from batch 2 had higher fat content of 9.5% with high Fiber weight % of 12.4%, compared to lower fat content of 9.1% for Big DDGS from batch 1 with low Fiber weight % of 8.4% (Table 22).

Pan DDGS, Enhanced DDGS and Big DDGS had lower NDF content than their source of original DDGS because of fiber removal (Table 22). For the same DDGS source, Pan DDGS had the lowest NDF, Enhanced DDGS had the next lowest NDF and Big DDGS had the highest NDF. Fiber (NDF) contents for Big DDGS and Enhanced were lower when higher weight % of Fiber was removed from the same DDGS. For example; for DDGS-1, Big DDGS had lower NDF content of 28.7% for batch 2 with high Fiber weight % of 15.3% compared to higher NDF content of 30.5% for Big DDGS from batch 1 with low Fiber weight % of 4.1% (Table 22).

NDF of Fiber from the DDGS varied from 43.6 to 53.2% (Table 22). NDF of pericarp and endosperm fiber from corn wet milling were 79.7 and 27.0%, respectively (Srinivasan, 2006). Thus, Fiber product from the Elusieve process has higher NDF than endosperm fiber from wet milling and lower NDF than pericarp fiber from wet milling. NDF contents for Fiber were higher when lower weight % of Fiber was produced from the same DDGS (Table 22). For example; for DDGS-1, Fiber had NDF content of 53.6% for batch 1 (low Fiber weight % of 4.1%), which was higher compared to NDF content of 45.7% for Fiber from batch 2 (high Fiber weight % of 15.3%).

Operating Experience

It was cumbersome to determine the lighter fraction yields from each sieve fraction by monitoring the weight of the collection drums for the lighter and heavier fractions over a fixed period of time. Installation of solids flow measuring devices to determine and control the yields of fractions would simplify operation and this is envisaged in future operations.

There were a few big chunks of foreign matter in DDGS-3. When DDGS-3 was processed for the first time, these big chunks blocked the feeding section of the multi-aspirator for the A sieve fraction (largest size) and caused an overflow of material out of the multi-aspirator. In subsequent operations, the feeding section of the multi-aspirator for the A sieve fraction was closely monitored and the chunks were removed before any blockage could occur. For industrial scale operation, the feeding section of the multi-aspirator for the A sieve fraction would need to be designed such that even large chunks would flow through.

To maintain the lighter fraction yield at the desired level, the butterfly damper in the air duct of the multi-aspirator that was used to aspirate the C sieve fraction had to be further opened during operation, while processing large quantity of DDGS (1096 kg for DDGS-3 batch 2). This occurred perhaps because of increased resistance to air flow from the filter bag due to accumulation of fine particles in the filter bag. This phenomenon was not observed in the other two multi-aspirators perhaps because of fewer fine particles in the A and B sieve fractions.

Implementation Scenario for the Elusieve Process and Economics

In the previous works on Elusieve process, it was suggested that two products would be produced; 1) Enhanced DDGS that had 2 to 3% higher protein content on wet basis than conventional DDGS and 2) Fiber product. As protein content plays a significant role in market value of feeds, we expect that the best implementation scenario for the Elusieve process would be to produce three products; 1) a product (Pan DDGS) that would have 5% higher protein content than the conventional DDGS on wet basis, 2) a product (Big DDGS) that would have nearly same protein content as conventional DDGS, and 3) Fiber product.

In the present market scenario, Elusieve products with higher protein contents are more valuable than products with higher fiber contents because conversion of fiber product into high-value products (cellulosic ethanol, corn fiber gum, polymer composites, etc) has not reached industrial scale yet. The implementation scenario with highest revenue potential is represented by DDGS-3 batch 2, where Pan DDGS has 4.8% higher protein content than original DDGS and Big DDGS has 0.7% lower protein content, but has higher fat and lower fiber contents, than original DDGS. The other operations, which result in products with higher fiber contents than higher protein contents, would be more beneficial when fiber value is high. The other operations are not considered the highest revenue scenarios due to the following reasons: 1) DDGS-1 batch 1: Pan DDGS does not have high protein content because the weight % of Pan DDGS is high (38.4%), 2) DDGS-1 batch 2: quantity of DDGS processed (53.5 kg) is low and hence, results may not be statistically suitable, 3) DDGS-2: Pan DDGS does not have high protein content because the weight % of Pan DDGS is high (47.8%), and 4) DDGS-1 batch 1: Big DDGS has low protein content, 1.5% lower than original DDGS, because of low weight % of Fiber removal due to low lighter fraction yields.

Price of Pan DDGS was determined using same method as Srinivasan et al. (2006), which was based on correlation between feed prices and their protein contents. Estimates of prices determined using this method is conservative because of not accounting for opening up of new markets for DDGS. For current prices of feeds obtained from ERS (2008), the increase in price of feed per percent increase in protein content was $7.20. Price of conventional DDGS at current prices was $160/ton and for the increase of 4.8% in protein content, the price of Pan DDGS was $195/ton (Table 23).

TABLE 23

Composition (% wb), weight % and price of products that represents the potential implementation scenario for the Elusieve process; obtained by pilot scale processing of DDGS-3 batch 2.

| Product | Weight % | Protein | Fat | NDF | Ash | Moisture | Price ($/ton) |
|---|---|---|---|---|---|---|---|
| Original DDGS | 100.0 | 30.4 | 7.3 | 25.6 | 4.0 | 12.3 | 160 |
| Enhanced DDGS | 87.6 | 31.8 | 7.7 | 23.7 | 4.1 | 12.2 | 170 |
| Big DDGS | 54.9 | 29.7 | 8.5 | 23.8 | 4.0 | 12.0 | 160 |
| Pan DDGS | 32.8 | 35.2 | 6.2 | 23.5 | 4.3 | 12.6 | 195 |
| Fiber | 12.4 | 20.4 | 5.0 | 38.8 | 3.5 | 12.5 | 114 |

Big DDGS was valued at the same price of $160/ton as conventional DDGS because Big DDGS has protein content close to conventional DDGS and has higher fat and lower fiber contents. Fiber product has 20.4% protein which is close to protein content of corn gluten feed (21% protein) and hence, Fiber product is valued at the same price of $114/ton as corn gluten feed. The increase in revenue, for a dry grind plant processing corn at 2,030 metric tonnes/day (80,000 bu/day), due to Elusieve products would be $1.4 million. Operating costs would be $100,000/yr based on energy consumption of 56 kW (75 hp) and labor requirement of 2 man hr/day (Srinivasan et al., 2006). There are no additional drying costs involved for implementation of the Elusieve process for DDGS. Capital investment would be $1.4 million based on $0.43 million as purchase cost of sifters and aspirators for the 2,030 metric tonnes/day (80,000 bu/day) plant (Srinivasan et al., 2006).

Payback period (in years) was calculated as total capital investment divided by profit per year (Peters et al., 1980). In calculating payback period, interest and depreciation effects were not accounted for. Net present value (NPV) was calculated by adding together the present values obtained from discounting the projected cash flows at an interest rate of 8% during the lifetime of the plant. The lifetime of the plant was assumed to be 15 years. Internal rate of return (IRR) is the interest rate at which the NPV of the projected cash flows becomes zero. For a 2,030 metric tonnes/day (80,000 bu/day) plant, based on revenue of $1.4 million, operating cost of $100,000/yr and capital investment of $1.4 million, the payback period for the Elusieve process would be 1.1 yr, IRR would be 91% and NPV would be $9.5 million. Financial returns decrease as plant capacity decreases. For a 1,520 metric tonnes/day (60,000 bu/day) plant, based on revenue of $1.0 million, operating cost of $75,000/yr and capital investment of $1.2 million, the payback period for the Elusieve process would be 1.2 yr, IRR would be 81% and NPV would be $7.0 million. For a 1,020 metric tonnes/day (40,000 bu/day) plant, based on revenue of $0.7 million, operating cost of $50,000/yr and capital investment of $0.9 million, the payback period for the Elusieve process would be 1.4 yr, IRR would be 69% and NPV would be $4.5 million.

Conclusions

A pilot plant for the Elusieve process to separate fiber from DDGS was assembled and operated in continuous mode with DDGS processing rate of 0.25 kg/s (1 ton/hr). Experiments were conducted on three different commercial DDGS materials. Elusieve process was effective in separating fiber from DDGS in pilot scale in continuous mode. Trends in compositions of fractions were similar to those observed in laboratory scale studies. Valuable operating experience was gained from pilot scale processing.

In the pilot scale operation that best represented the potential implementation scenario, 12.4% by weight of DDGS was separated as Fiber and resulted in two high protein products; 1) a product (Pan DDGS; 32.8% by weight) that had 4.8% higher protein content and lower fiber content than conventional DDGS, on wet basis and 2) a product (Big DDGS; 54.9% by weight) that had nearly same protein content (difference of −0.7%) as conventional DDGS, and had lower fiber (NDF) contents than conventional DDGS. Implementation of the Elusieve process in a dry grind plant processing corn at 2,030 metric tonnes/day (80,000 bu/day) would increase revenue by $1.4 million based on conservative estimates, operating cost would be $100,000/yr, capital investment required would be $1.4 million and the payback period would be 1.1 yr. In the context of the need for opening up of new markets and producing valuable products from DDGS, the Elusieve process offers a simple and non-intrusive method to add value to fuel ethanol production. The pilot plant assembled for the Elusieve process was useful in gaining operating experience and data needed for plant scale implementation.

References

AACC International. 2000. Approved Methods of the American Association of Cereal Chemists, 10th Ed. Methods 44-18 and 77-11. The Association: St. Paul, Minn., USA.

AOAC. 2003. Official Methods of Analysis of the Association of Official Analytical Chemists, 17th ed. Gaithersburg, M.D, USA.

Belyea, R. L., Rausch, K. D., Tumbleson, M. E., 2004. Composition of corn and distillers dried grains with solubles from dry grind ethanol processing. Biores. Technol. 94, 293-298.

Buhner, J. and Agblevor, F. A. 2004. Effect of detoxification of dilute acid corn fiber hydrolysate on xylitol production. Appl. Biochem. Biotechnol. 119:13-30.

Crittenden, R. G. and Playne, M. J. 1996. Production, properties and applications of food grade oligosaccharides. Trend Food Sci. Technol. 7:353-361.

Dien, B. S., Hespell, R. B., Ingram, L. O. and Bothast, R. J. 1997. Conversion of corn milling fibrous coproducts into ethanol by recombinant *Escherichia coli* strains K011 and SL40. World J. Microbiol. Biotechnol. 13:619-625.

Doner, L. W., Chau, H. K., Fishman, M. L. and Hicks, K. B. 1998. An improved process for isolation of corn fiber gum. Cereal Chem. 75:408-411.

ERS, 2008. Feed outlook report of Jul. 15, 2008. Economic Research Service, USDA. Washington, D.C.

Ileleji, K. E., Prakash, K. S., Stroshine, R. L., Clementson, C. L., 2007. An investigation of particle segregation in corn processed dried distillers grains with solubles (DDGS) induced by three handling scenarios. Bulk Solids & Powder—Sci. Technol. 2, 84-94.

Kim, E., Parsons, C., Singh, V., Srinivasan, R., 2007. Nutritional evaluation of new corn distillers dried grains with solubles (DDGS) produced by the enzymatic milling (E-Mill) and elusieve processes. Poult. Sci. Vol. 86, Suppl. 1, P 397.

Kim, E. J., Parsons, C. M., Srinivasan, R. and Singh, V. 2010. Nutritional composition, nitrogen-corrected true metabolizable energy, and amino acid digestibilities of new corn distillers dried grains with solubles produced by new fractionation processes. J. Poultry Sci. 89:44-51.

Liu, K. 2009. Fractionation of distillers dried grains with solubles (DDGS) by sieving and winnowing. Biores. Technol. 100: 6559-6569.

Loar, R., Srinivasan, R., Kidd, M., Dozier, W. and Corzo, A. 2009. Effects of elutriation and sieving processing (Elusieve) of distillers dried grains with solubles on the performance and carcass characteristics of male broilers. J. Appl. Poultry Res. 18:494-500.

Loar, R. E., Srinivasan, R., Dozier, W. A. III, Kidd, M. T., Corzo, A., 2008. Impact of fiber separation on the nutritional value of distillers dried grains with solubles in broiler diet. Poult. Sci. Vol. 87, Suppl. 1, P 28.

Martinez-Amezuca, C., Parsons, C. M., Singh, V., Srinivasan, R., Murthy, G. S., 2007. Nutritional characteristics of corn distillers dried grains with solubles as affected by amounts of grains versus solubles and different processing techniques. J. Poultry Sci. 86, 2624-2630.

Moreau, R. A., Powell, M. J. and Hicks, K. B. 1996. Extraction and quantitative analysis of oil from commercial corn fiber. J. Agric. Food Chem. 44:2149-2154.

NDSU. 1999. Wheat Middlings: Feeds and feeding educational materials. North Dakota State University, Fargo, N. Dak. http://www.ag.ndsu.edu/pubs/ansci/livestoc/as1175w.htm.

Noll, S., Stangeland, V., Speers, G., Brannon, J., 2001. Distillers grains in poultry diets. 62nd Minnesota Nutrition Conference and Minnesota Corn Growers Association Technical Symposium, Bloomington, Minn.

NRC. 1994. Nutrient requirements of poultry. 9th ed. National Academy Press, Washington D.C.

Peters, M. S, and Timmerhaus, K. D. 1980. Plant Design and Economics for Chemical Engineers, 3rd. McGraw-Hill: New York, N.Y.

RFA, 2008. U.S. fuel ethanol production capacity. Renewable Fuels Association. www.ethanolrfa.org/industry/statistics. July, 2008. Washington, D.C.

Rosentrater, K. A., 2008. Ethanol processing coproducts—economics, impacts, sustainability. Proc. National Agricultural Biotechnology Council's 19th Annual Conference, Brookings S. Dak. May 22-24, 2007:105-126.

Shurson, G. C., 2002. The value and use of distiller's dried grains with solubles (DDGS) in swine diets. Carolina Nutrition Conference, Raleigh, N.C.

SMIC. 2008. Soybean meal info center, Urbandale, Iowa. September 2008, www.soymeal.org.

Soares, J. A. 2009. Nutrient value of distillers co-products fed to pigs. MS Thesis. University of Illinois.

Srinivasan, R., 2006. Separation of fiber from distillers dried grains with solubles using sieving and elutriation. PhD dissertation. Department of Agricultural and Biological Engineering, University of Illinois: Urbana, Ill.

Srinivasan, R., Challa, R. K., Hicks, K. B., Wilson, J., Kurantz, M., Moreau, R. A. 2009. Fractionation of barley flour using combination of sieving and air classification. Cereal Chemistry (submitted to Cereal Chem).

Srinivasan, R., Moreau, R. A., Rausch, K. D., Belyea, R. L., Tumbleson, M. E. and Singh, V. 2005. Separation of fiber from distillers dried grains with solubles (DDGS) using sieving and elutriation. Cereal Chem. 82:528-533.

Srinivasan, R., and Singh, V. 2008a. Pericarp Fiber Separation from Corn Flour Using Sieving and Air Classification. Cereal Chem. 85:27-30.

Srinivasan, R. and Singh, V. 2008b. Physical properties that govern fiber separation from distillers dried grains with solubles (DDGS) using sieving and air classification. Separation and Purification Technol. 61:461-468.

Srinivasan, R., Singh, V., Belyea, R. L., Rausch, K. D., Moreau, R. A. and Tumbleson, M. E. 2006. Economics of fiber separation from distillers dried grains with solubles (DDGS) using sieving and elutriation. Cereal Chem. 83:324-330.

Srinivasan, R., To, F. and Columbus, E. 2009. Pilot scale fiber separation from distillers dried grains with solubles (DDGS) using sieving and air classification. Bioresource Technol. 100:3548-3555.

Srinivasan, R., Yadav, M. P., Belyea, R. L., Rausch, K. D., Pruiett, L. E., Johnston, D. B., Tumbleson, M. E. and Singh, V. 2008. Fiber separation from distillers dried grains with solubles (DDGS) using a larger elutriation apparatus and use of fiber as a feedstock for corn fiber gum. Biol. Engg. 1:39-49.

Sundberg, B., Tilly, A. C., Aman, P. 1995. Enrichment of mixed linked (1→3), (1→4)-β-D-glucans from a high-fiber barley-milling stream by air classification and stack-sieving. J. Cereal Sci. 21, 205-208.

USDA-NASS. 2009. United States Department of Agriculture—National agricultural statistics service, Washington, D.C. February 2009, www.nass.usda.gov/QuickStats/.

Van Soest, P. J., Robertson, J. B., Lewis, B. A. 1991. Methods for dietary fiber, neutral detergent fiber and non-starch polysaccharides in relation to animal nutrition. J. Dairy Sci. 74, 3583-3597.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques, other than those specifically described herein, can be applied to the practice of the invention as broadly disclosed herein without resorting to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents, including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A method of generating a fiber-reduced fraction and a fiber enriched fraction from a grain, comprising:
   a) processing the grain to produce a dry starting material;
   b) separating by size dry starting material into a first fraction and a second fraction, wherein said first fraction has a larger particle size, and said second fraction has a smaller particle size;
   c) collecting said second fraction;
   d) air classifying said first fraction so as to yield a first subfraction of a lighter material enriched in fiber relative to said first fraction and a second subfraction of a heavier material reduced in fiber relative to said first fraction; and
   e) collecting said second subfraction, wherein said second subfraction is reduced in fiber relative to said dry starting material; thereby generating the fiber-reduced fraction and the fiber-enriched fraction.

2. The method of claim 1 further comprising combining said second fraction of smaller particle size and said second subfraction, thereby forming a combined material reduced in fiber relative to said starting material.

3. The method of claim 2 wherein said combined material has a fiber content of 10% or less.

4. The method of claim 2 wherein said combined material is enriched in protein content, fat content, or both protein and fat content relative to said starting material.

5. The method of claim 1 further comprising a second air classifying by gravity air elutriation of said second fraction of smaller particle size so as to yield a third subfraction of a lighter material enriched in fiber and a fourth subfraction of a heavier material reduced in fiber relative to said second fraction.

6. The method of claim 5 further comprising combining said fourth subfraction and said second subfraction, thereby forming a combined material reduced in fiber relative to said starting material.

7. The method of claim 6 wherein said combined material has increased fat and protein concentration relative to said starting material.

8. The method of claim 5 further comprising combining said first subfraction with said third subfraction, thereby forming a combined material enriched in fiber relative to said starting material.

9. A method of generating a fiber reduced fraction from a starting material selected from the list comprising of ground corn flour, soybean meal, cottonseed meal, and wheat middlings comprising:
   a) separating by size said starting material into a first fraction and a second fraction, wherein said first fraction has a larger particle size, and said second fraction has a smaller particle size and is reduced in fiber in relation to said starting material;
   c) air classifying said second fraction so as to yield a first subfraction of a lighter material enriched in fiber relative to said second fraction and a second subfraction of a heavier material reduced in fiber relative to said second fraction; and
   d) collecting said second subfraction, wherein said second subfraction is reduced in fiber relative to said starting material; thereby generating the fiber-reduced fraction.

10. The method of claim 9 wherein said collected second subfraction has a fiber content of 10% or less.

11. The method of claim 9 wherein said combined second subfraction is enriched in protein content, fat content, or both protein and fat content relative to said starting material.

12. The method of claim 9 further comprising air classifying said first fraction using gravity air elutriation so as to yield a third subfraction of a lighter material enriched in fiber and a fourth subfraction of a heavier material reduced in fiber relative to said first fraction.

13. The method of claim 12 further comprising combining said fourth subfraction and said second subfraction, thereby forming a combined material reduced in fiber relative to said starting material.

14. The method of claim 12 further comprising combining said first fraction and said third subfraction, thereby forming a combined material enriched in fiber relative to said starting material.

15. The method of claim 9 wherein said air classifying step employs an air classification system selected from the group consisting of: static cyclone, cyclone classifiers, single or multi-stage dynamic classifiers, cross-flow classifiers, spiral separators, high energy dispersion classifiers, and turbine classifiers (single and multiple wheel).

* * * * *